United States Patent
Budde et al.

(10) Patent No.: US 11,433,009 B2
(45) Date of Patent: *Sep. 6, 2022

(54) SURFACE-REACTED CALCIUM CARBONATE FOR THE USE AS SKIN APPEARANCE MODIFIER

(71) Applicant: OMYA INTERNATIONAL AG, Oftringen (CH)

(72) Inventors: Tanja Budde, Brittnau (CH); Anaïs Hecker, Oftringen (CH)

(73) Assignee: OMYA INTERNATIONAL AG, Oftringen (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/961,312

(22) PCT Filed: Jan. 23, 2019

(86) PCT No.: PCT/EP2019/051651
§ 371 (c)(1),
(2) Date: Jul. 10, 2020

(87) PCT Pub. No.: WO2019/145369
PCT Pub. Date: Aug. 1, 2019

(65) Prior Publication Data
US 2021/0077368 A1    Mar. 18, 2021

(30) Foreign Application Priority Data

Jan. 26, 2018 (EP) ..................................... 18153726

(51) Int. Cl.
| | | |
|---|---|---|
| *A61K 8/19* | (2006.01) | |
| *A61K 8/02* | (2006.01) | |
| *A61Q 1/06* | (2006.01) | |
| *A61Q 1/10* | (2006.01) | |
| *A61Q 1/12* | (2006.01) | |
| *A61Q 19/00* | (2006.01) | |

(52) U.S. Cl.
CPC .............. *A61K 8/19* (2013.01); *A61K 8/0229* (2013.01); *A61K 8/0241* (2013.01); *A61Q 1/06* (2013.01); *A61Q 1/10* (2013.01); *A61Q 1/12* (2013.01); *A61Q 19/00* (2013.01); *A61K 2800/412* (2013.01); *A61K 2800/61* (2013.01)

(58) Field of Classification Search
None
See application file for complete search history.

(56) References Cited

U.S. PATENT DOCUMENTS

| | | | |
|---|---|---|---|
| 6,004,584 A | 12/1999 | Peterson et al. | |
| 6,165,510 A | 12/2000 | Baines et al. | |
| 6,461,626 B1 | 10/2002 | Rabe et al. | |
| 9,144,434 B1 | 9/2015 | Rodan et al. | |
| 9,593,244 B2 | 3/2017 | Gane et al. | |
| 2004/0020410 A1 | 2/2004 | Gane et al. | |
| 2015/0218381 A1 | 8/2015 | O'Halloran et al. | |
| 2015/0290094 A1* | 10/2015 | Izumikawa | C01F 11/18 424/401 |
| 2016/0271025 A1* | 9/2016 | Budde | A61K 8/19 |

FOREIGN PATENT DOCUMENTS

| | | |
|---|---|---|
| EP | 0173391 A2 | 3/1986 |
| EP | 1712523 A1 | 10/2006 |
| EP | 1712597 A1 | 10/2006 |
| EP | 2168572 A1 | 3/2010 |
| EP | 2264108 A1 | 12/2010 |
| EP | 2264109 A1 | 12/2010 |
| EP | 2371766 A1 | 10/2011 |
| EP | 2447213 A1 | 5/2012 |
| EP | 2524898 A1 | 11/2012 |
| EP | 2883573 A1 | 6/2015 |
| EP | 2910237 A1 | 8/2015 |
| EP | 3045503 A1 | 7/2016 |
| EP | 2245095 B1 | 2/2017 |
| KR | 20030062371 | 7/2003 |
| WO | 00/39222 A1 | 7/2000 |
| WO | 2004/083316 A1 | 9/2004 |
| WO | 2005/121257 A2 | 12/2005 |
| WO | 2009/074492 A1 | 6/2009 |
| WO | 2013/142473 A1 | 9/2013 |

OTHER PUBLICATIONS

International Search Report from PCT/EP2019/051651, dated Mar. 11, 2019, 4 pages.
Written Opinion from PCT/EP2019/051651, dated Mar. 11, 2019, 7 pages.
International Search Report from PCT/EP2019/051656, dated Mar. 15, 2019, 3 pages.
Written Opinion from PCT/EP2019/051656, dated Mar. 15, 2019, 6 pages.
Gane et al. (1996) "Void Space Structure of Compressible Polymer Spheres and Consolidated Calcium Carbonate Paper-Coating Formulations" Ind. Eng. Chem. Res., vol. 35, pp. 1753-1764.
Regulation (EC) No. 1223/2009 of the European Parliament and of the Council of Nov. 30, 2009 on Cosmetic Products (151 pages).
U.S. Appl. No. 16/961,671 nonfinal Office action dated Jun. 4, 2021, 25 pages.
U.S. Appl. No. 16/961,671 Response to nonfinal Office action dated Aug. 22, 2021, 11 pages.
U.S. Appl. No. 16/961,671 final Office action dated Aug. 31, 2021, 26 pages.
U.S. Appl. No. 16/961,671 Response to nonfinal Office action dated Nov. 30, 2021, 12 pages.
U.S. Appl. No. 16/961,671 nonfinal Office action dated Mar. 17, 2021, 11 pages.
U.S. Appl. No. 16/961,671 Response to nonfinal Office action dated May 29, 0222, 8 pages.
KR20030062371 (Jul. 25, 2003), English language translation of publication, 6 pages.

(Continued)

*Primary Examiner* — Melissa L Fisher
(74) *Attorney, Agent, or Firm* — ALGM LLP; Harry J. Guttman

(57) ABSTRACT

The present invention refers to the use of a surface-reacted calcium carbonate having a volume median particle size $d_{50}$ from 0.1 to 90 μm as skin appearance modifier in a cosmetic and/or skin care composition.

21 Claims, No Drawings

(56) References Cited

OTHER PUBLICATIONS

Deckner (2014) "Finding Alternatives to Synthetic Exfoliating Beads" posted at www.Knowledge.ULProspector.com, last accessed Nov. 17, 2016. 3 pages.

* cited by examiner

SURFACE-REACTED CALCIUM CARBONATE FOR THE USE AS SKIN APPEARANCE MODIFIER

CROSS-REFERENCE TO RELATED APPLICATIONS

This application is a National Stage Entry of International Application No. PCT/EP2019/051651 filed Jan. 23, 2019, entitled "SURFACE-REACTED CALCIUM CARBONATE FOR THE USE AS SKIN APPEARANCE MODIFIER", and which claims priority to EP Application No 18153726.7 filed Jan. 26, 2018 entitled "SURFACE-REACTED CALCIUM CARBONATE FOR THE USE AS SKIN APPEARANCE MODIFIER."

The present invention refers to the use of a surface-reacted calcium carbonate having a volume median particle size $d_{50}$ from 0.1 to 90 μm as a skin appearance modifier in a cosmetic and/or skin care composition.

A variety of cosmetic composition are available for the application onto the skin of the face and/or the body. Often such compositions are applied to modify the appearance of the skin, for example, in order to hide blemishes, conceal or diminish fine lines or wrinkles, minimize pores or to change and/or even out the skin tone. Certain cosmetic compositions are also capable to control the skin sheen to a certain extend by absorbing/adsorbing sebum, and thereby providing the skin with a mat gloss. In addition to these optical effects, it is often desirable that a cosmetic composition provides the user with a natural, or ideally with a more pleasant, skin feel. A natural or positive skin feel is often associated with a smooth, fresh and/or elastic skin sensation and a skin surface which does not feel greasy or dry.

Several cosmetic compositions and/or skin care compositions are known in the prior art. Exemplarily, reference is made to U.S. Pat. No. 6,461,626 B1 which refers to a wear resistant topical composition having improved feel. The patent discloses substantially uniform, discontinuous films of a topical product having a defined abrasion resistance, coverage value and particle spacing. U.S. Pat. No. 6,165,510 discloses a cosmetic composition including an inorganic material in granular form which, under conditions of use of the cosmetic composition, breaks down to a particle size, wherein less than 5% by weight is above 45 microns, as measured by wet sieve analysis. Furthermore, U.S. Pat. No. 6,004,584 relates to moisture absorbing body powder compositions. The powder carrier which provides good skin feel characteristics comprises skin feel components selected from the group consisting of: starch, metallic stearates, fatty acid derivatives, nylon, polyethylene, polytetrafluoroethylene, and platelet-shaped powders. EP 0 173 391 A2 refers to a skin cleansing composition comprising a soap or synthetic detergent and finely divided alkaline earth metal carbonates. The alkaline earth metal carbonates produce frictional forces on the wet rinsed skin which users associate with a feeling of cleanliness.

To provide a cosmetic and/or skin care composition with some of the above-mentioned properties, synthetic or mineral powders or fillers such as talc, mica, silica or titanium dioxide are often added as opacifying or covering agents to such compositions. However, for some cosmetic and/or skin care compositions the use of such powders or fillers can lead to an unnatural or artificial look, especially if the composition contains large amounts of such powders or fillers. For other cosmetic and/or skin care compositions the opacifying or covering effect can be low and skin lines may even be accentuated after their application. Furthermore, the application of such cosmetic and/or skin care composition onto the skin can be accompanied by an unusual or negative skin feel which manifests, for example, in a dry or oily feeling and/or stiff or tight skin sensation.

In view of the foregoing, there is still a demand for a skin appearance modifier for the use in cosmetic and/or skin care compositions. In particular, there is a demand for a skin appearance modifier for the use in cosmetic and/or skin care compositions such that wrinkles and/or skin imperfections are effectively hidden or concealed. Furthermore, a skin appearance modifier for the use in cosmetic products is required that provides the skin with a natural and/or mattified look. There is also a demand for a skin appearance modifier for the use in cosmetic and/or skin care compositions that provides the skin with a positive skin feel, and especially with a smooth and/or fresh skin sensation.

Accordingly, an objective of the present invention may be seen in the provision of a skin appearance modifier for the use in a cosmetic and/or skin care composition, and especially for the use in cosmetic and/or skin care compositions which are used to conceal or hide wrinkles and/or skin imperfections. Another objective of the present application is the provision of a skin appearance modifier for the use in a cosmetic and/or skin care composition which provides the skin with a natural and/or mattified look. Yet another objective may be seen in the provision of a skin appearance modifier for the use in a cosmetic and/or skin care composition that provides the skin with a positive skin feel, and especially with a smooth and/or fresh skin sensation.

One or more of the foregoing objectives is/are solved by the present invention.

According to one aspect of the present invention, the use of a surface-reacted calcium carbonate having a volume median particle size $d_{50}$ from 0.1 to 90 μm as skin appearance modifier in a cosmetic and/or skin care composition is provided. The surface-reacted calcium carbonate is a reaction product of natural ground calcium carbonate or precipitated calcium carbonate with carbon dioxide and one or more $H_3O^+$ ion donors, wherein the carbon dioxide is formed in situ by the $H_3O^+$ ion donors treatment and/or is supplied from an external source Advantageous embodiments of the inventive use are defined in the corresponding sub-claims.

According to one embodiment of the present invention, the surface-reacted calcium carbonate has a volume median particle size $d_{50}$ from 0.5 to 50 μm, preferably from 1 to 40 μm, more preferably from 1.2 to 30 μm, and most preferably from 1.5 to 15 μm.

According to another embodiment of the present invention, the surface-reacted calcium carbonate has a specific surface area of from 15 m²/g to 200 m²/g, preferably from 20 m²/g to 180 m²/g, and most preferably from 25 m²/g to 160 m²/g, measured using nitrogen and the BET method.

According to yet another embodiment of the present invention, the natural ground calcium carbonate is selected from the group consisting of marble, chalk, limestone, and mixtures thereof, or the precipitated calcium carbonate is selected from the group consisting of precipitated calcium carbonates having an aragonitic, vateritic or calcitic crystal form, and mixtures thereof.

According to one embodiment of the present invention, the at least one $H_3O^+$ ion donor is selected from the group consisting of hydrochloric acid, sulphuric acid, sulphurous acid, phosphoric acid, citric acid, oxalic acid, an acidic salt, acetic acid, formic acid, and mixtures thereof, preferably the at least one $H_3O^+$ ion donor is selected from the group consisting of hydrochloric acid, sulphuric acid, sulphurous acid, phosphoric acid, oxalic acid, $H_2PO_4^-$, being at least partially neutralised by a cation selected from $Li^+$, $Na^+$ and/or $K^+$, $HPO_4^{2-}$, being at least partially neutralised by a cation selected from $Li^+$, $Na^+$, $K^+$, $Mg^{2+}$, and/or $Ca^{2+}$, and mixtures thereof, more preferably the at least one $H_3O^+$ ion donor is selected from the group consisting of hydrochloric acid, sulphuric acid, sulphurous acid, phosphoric acid, oxalic acid, or mixtures thereof, and most preferably, the at least one $H_3O^+$ ion donor is phosphoric acid.

According to another embodiment of the present invention, the skin appearance modifier is a covering agent, a mattifying agent and/or a skin colour modifier, and preferably a covering agent and/or a mattifying agent.

According to another embodiment of the present invention, the cosmetic and/or skin care composition has a pH value of ≤8.5, preferably ≤8.0, more preferably preferably ≤7.0, and most preferably from 4.0 to 7.0.

According to yet another embodiment of the present invention, the surface-reacted calcium carbonate is present in the cosmetic and/or skin care composition in an amount from 0.1 to 50 wt.-%, based on the total weight of the composition, preferably from 0.5 to 20 wt.-%, more preferably from 1 to 10 wt.-%, and most preferably from 3 to 10 wt.-%.

According to one embodiment of the present invention, the cosmetic and/or skin care composition further comprises water and/or at least one oil, preferably the at least one oil is selected from the group consisting of vegetable oils and esters thereof, alkanecoconutester, plant extracts, animal fats, siloxanes, silicones, fatty acids and esters thereof, petrolatum, glycerides and pegylated derivatives thereof, and mixtures thereof.

According to another embodiment of the present invention, the cosmetic and/or skin care composition comprises at least one active agent being absorbed onto and/or adsorbed into the surface of the surface-reacted calcium carbonate.

According to yet another embodiment of the present invention, the at least one active agent is selected from pharmaceutically active agents, biologically active agents, vitamins, disinfecting agents, preservatives, flavouring agents, surfactants, oils, fragrances, essential oils, and mixtures thereof.

According to one embodiment of the present invention, the composition further comprises at least one additive selected from the group consisting of bleaching agents, thickeners, stabilizers, chelating agents, preserving agents, wetting agents, emulsifiers, emollients, fragrances, colorants, skin tanning compounds, antioxidants, minerals, pigments, UV-A and/or UV-B filter, and mixtures thereof.

According to another embodiment of the present invention, the cosmetic and/or skin care composition is selected from an eye make-up product, a facial make-up product, a lip care product, a hand care product, a skin care product, or a combination product thereof.

According to yet another embodiment of the present invention, the cosmetic and/or skin care composition has a Brookfield viscosity in a range from 4 000 to 50 000, preferably from 10 000 to 45 000, more preferably from 15 000 to 40 000, even more preferably from 20 000 to 40 000, and most preferably from 25 000 to 40 000 mPa·s at 25° C.

According to one embodiment of the present invention, the surface-reacted calcium carbonate further provides skin feel modification.

It should be understood that for the purposes of the present invention, the following terms have the following meanings:

A "cosmetic and/or skin care" composition in the meaning of the present invention refers to a composition that is applied onto the skin. That is to say, a "cosmetic and/or skin care" composition does not encompass a composition that is typically taken up orally.

"Natural ground calcium carbonate" (GCC) in the meaning of the present invention is a calcium carbonate obtained from natural sources, such as limestone, marble, or chalk, and processed through a wet and/or dry treatment such as grinding, screening and/or fractionating, for example, by a cyclone or classifier.

"Precipitated calcium carbonate" (PCC) in the meaning of the present invention is a synthesised material, obtained by precipitation following reaction of carbon dioxide and lime in an aqueous, semi-dry or humid environment or by precipitation of a calcium and carbonate ion source in water. PCC may be in the vateritic, calcitic or aragonitic crystal form. PCCs are described, for example, in EP 2 447 213 A1, EP 2 524 898 A1, EP 2 371 766 A1, EP 1 712 597 A1, EP 1 712 523 A1, or WO 2013/142473 A1.

The term "surface-reacted" in the meaning of the present application shall be used to indicate that a material has been subjected to a process comprising partial dissolution of said material upon treatment with an $H_3O^+$ ion donor (e.g., by use of water-soluble free acids and/or acidic salts) in aqueous environment followed by a crystallization process which may occur in the absence or presence of further crystallization additives.

An "$H_3O^+$ ion donor" in the context of the present invention is a Brønsted acid and/or an acid salt, i.e. a salt containing an acidic hydrogen.

The term "acid" as used herein refers to an acid in the meaning of the definition by Brønsted and Lowry (e.g., $H_2SO_4$, $HSO_4^-$).

The term "free acid" refers only to those acids being in the fully protonated form (e.g., $H_2SO_4$).

The "particle size" of particulate materials other than surface-reacted calcium carbonate herein is described by its distribution of particle sizes $d_x$. Therein, the value $d_x$ represents the diameter relative to which x % by weight of the particles have diameters less than $d_x$. This means that, for example, the $d_{20}$ value is the particle size at which 20 wt.-% of all particles are smaller than that particle size. The $d_{50}$ value is thus the weight median particle size, i.e. 50 wt.-% of all particles are smaller than this particle size. For the purpose of the present invention, the particle size is specified as weight median particle size $d_{50}$ (wt.) unless indicated otherwise. Particle sizes were determined by using a Sedigraph™ 5100 instrument or Sedigraph™ 5120 instrument of Micromeritics Instrument Corporation. The method and the instrument are known to the skilled person and are commonly used to determine the particle size of fillers and pigments. The measurements were carried out in an aqueous solution of 0.1 wt.-% $Na_4P_2O_7$.

The "particle size" of surface-reacted calcium carbonate herein is described as volume-based particle size distribution. Volume median particle size $d_{50}$ was evaluated using a Malvern Mastersizer 2000 Laser Diffraction System. The $d_{50}$ or $d_{98}$ value, measured using a Malvern Mastersizer 2000 Laser Diffraction System, indicates a diameter value such that 50% or 98% by volume, respectively, of the particles have a diameter of less than this value. The raw data obtained by the measurement are analysed using the Mie theory, with a particle refractive index of 1.57 and an absorption index of 0.005.

The term "particulate" in the meaning of the present application refers to materials composed of a plurality of particles. Said plurality of particles may be defined, for example, by its particle size distribution. The expression "particulate material" may comprise granules, powders, grains, tablets, or crumbles.

The "specific surface area" (expressed in m²/g) of a material as used throughout the present document can be determined by the Brunauer Emmett Teller (BET) method with nitrogen as adsorbing gas and by use of a ASAP 2460 instrument from Micromeritics. The method is well known to the skilled person and defined in ISO 9277:2010. Samples are conditioned at 100° C. under vacuum for a period of 30 min prior to measurement. The total surface area (in m²) of said material can be obtained by multiplication of the specific surface area (in m²/g) and the mass (in g) of the material.

In the context of the present invention, the term "pore" is to be understood as describing the space that is found between and/or within particles, i.e. that is formed by the particles as they pack together under nearest neighbour contact (interparticle pores), such as in a powder or a compact and/or the void space within porous particles (intraparticle pores), and that allows the passage of liquids under pressure when saturated by the liquid and/or supports absorption of surface wetting liquids.

The term "skin appearance modifier" in the meaning of the present invention refers to a cosmetic ingredient which is used to modify the appearance of the skin surface. For example, the appearance of the skin surface may be modified by covering the skin surface, mattifying the skin surface and/or modifying the skin colour. Thus, the use of a surface-reacted calcium carbonate as described herein as a skin appearance modifier comprises the use of the surface-reacted calcium carbonate as described herein as a covering agent, mattifying agent and/or skin colour modifier. The term "skin appearance modifier" is not meant to encompass the modification of biomechanical properties of the skin such as elasticity.

The term "covering agent" in the meaning of the present invention refers to a cosmetic ingredient which is used to cover and/or opacify the skin surface, for example, to conceal skin imperfections and/or wrinkles. The covering power, i.e. the power of the covering agent to cover and/or to opacify the skin surface, can be measured by spreading a cosmetic and/or skin care compositions comprising the covering agent on a contrast paper and subsequently measuring the colour values Rx, Ry, Rz of the composition by the means of a colorimeter. By comparison of the colour values of the cosmetic composition and that of the contrast paper, the contrast is calculated. The contrast directly refers to the covering power. Contrast ratio values are determined according to ISO 2814 at a spreading rate of approx. 20 m²/l. The contrast ratio is calculated as described by the equation below:

$$\text{Contrast ratio } [\%] = \frac{Ry_{black}}{Ry_{white}} \times 100\%$$

with $Ry_{black}$ and $Ry_{white}$ being obtained by the measurement of the colour values.

The expression "mattifying agent" in the meaning of the present invention refers to a cosmetic ingredient which is used to decrease the gloss and/or shininess of the skin surface, for example, by sebum absorption and/or regulation of sebum production. The mattifying power, i.e. the power of the mattifying agent to decrease the gloss and/or shininess of the skin surface, can be measured by using e.g. a Skin-Glossymeter® GL200 probe as described in the examples.

The "skin feel" of a cosmetic and/or skin care composition refers to the skin feeling that is perceived by the applicant during the application of the cosmetic and/or skin care composition onto the skin surface. The term is also meant to encompass the skin feeling that is perceived by the applicant shortly after the application of the cosmetic and/or skin care composition onto the skin surface, i.e. up to 5 minutes after the application of the cosmetic and/or skin care composition.

The expression "skin feel modification" in the meaning of the present invention refers to the modification of the skin feel as described above after application of the cosmetic and/or skin care composition. Skin feel modification relates to, for example, reduced dry time of the composition when applied on the skin or a reduction of the greasiness of the composition when applied on the skin. Furthermore, skin feel modification may also relate to the fluidity, spreadability, homogeneity, tack and/or resistance of the composition when applied to the skin.

Unless specified otherwise, the term "drying" refers to a process according to which at least a portion of water is removed from a material to be dried such that a constant weight of the obtained "dried" material at 120° C. is reached. Moreover, a "dried" or "dry" material may be defined by its total moisture content which, unless specified otherwise, is less than or equal to 1.0 wt.-%, preferably less than or equal to 0.5 wt.-%, more preferably less than or equal to 0.2 wt.-%, and most preferably between 0.03 and 0.07 wt.-%, based on the total weight of the dried material.

For the purpose of the present application, "water-insoluble" materials are defined as those which, when mixed with 100 ml of deionised water and filtered at 20° C. to recover the liquid filtrate, provide less than or equal to 0.1 g of recovered solid material following evaporation at 95 to 100° C. of 100 g of said liquid filtrate. "Water-soluble" materials are defined as materials leading to the recovery of greater than 0.1 g of solid material following evaporation at 95 to 100° C. of 100 g of said liquid filtrate. In order to assess whether a material is an insoluble or soluble material in the meaning of the present invention, the sample size is greater than 0.1 g, preferably 0.5 g or more.

A "suspension" or "slurry" in the meaning of the present invention comprises undissolved solids and water, and optionally further additives, and usually contains large amounts of solids and, thus, is more viscous and can be of higher density than the liquid from which it is formed.

Where an indefinite or definite article is used when referring to a singular noun, e.g., "a", "an" or "the", this includes a plural of that noun unless anything else is specifically stated.

Where the term "comprising" is used in the present description and claims, it does not exclude other elements. For the purposes of the present invention, the term "consisting of" is considered to be a preferred embodiment of the term "comprising". If hereinafter a group is defined to comprise at least a certain number of embodiments, this is also to be understood to disclose a group, which preferably consists only of these embodiments.

Terms like "obtainable" or "definable" and "obtained" or "defined" are used interchangeably. This, for example, means that, unless the context clearly dictates otherwise, the term "obtained" does not mean to indicate that, for example, an embodiment must be obtained by, for example, the sequence of steps following the term "obtained" though such a limited understanding is always included by the terms "obtained" or "defined" as a preferred embodiment.

Whenever the terms "including" or "having" are used, these terms are meant to be equivalent to "comprising" as defined hereinabove.

In the following preferred embodiments of the inventive composition will be set out in more detail.

Surface-Reacted Calcium Carbonate

The present invention refers to the use of a surface-reacted calcium carbonate having a volume median particle size $d_{50}$ from 0.1 to 90 μm as skin appearance modifier in a cosmetic and/or skin care composition, wherein the surface-reacted calcium carbonate is a reaction product of natural ground calcium carbonate or precipitated calcium carbonate with carbon dioxide and one or more $H_3O^+$ ion donors, wherein the carbon dioxide is formed in situ by the $H_3O^+$ ion donors treatment and/or is supplied from an external source.

In a preferred embodiment of the invention the surface-reacted calcium carbonate is obtained by a process comprising the steps of: (a) providing a suspension of natural or precipitated calcium carbonate, (b) adding at least one acid having a $pK_a$ value of 0 or less at 20° C. or having a $pK_a$ value from 0 to 2.5 at 20° C. to the suspension of step a), and (c) treating the suspension of step (a) with carbon dioxide before, during or after step (b). According to another embodiment the surface-reacted calcium carbonate is obtained by a process comprising the steps of: (A) providing a natural or precipitated calcium carbonate, (B) providing at least one water-soluble acid, (C) providing gaseous $CO_2$, (D) contacting said natural or precipitated calcium carbonate of step (A) with the at least one acid of step (B) and with the $CO_2$ of step (C), characterised in that: (i) the at least one acid of step B) has a $pK_a$ of greater than 2.5 and less than or equal to 7 at 20° C., associated with the ionisation of its first available hydrogen, and a corresponding anion is formed on loss of this first available hydrogen capable of forming a water-soluble calcium salt, and (ii) following contacting the at least one acid with natural or precipitated calcium carbonate, at least one water-soluble salt, which in the case of a hydrogen-containing salt has a $pK_a$ of greater than 7 at 20° C., associated with the ionisation of the first available hydrogen, and the salt anion of which is capable of forming water-insoluble calcium salts, is additionally provided.

"Natural ground calcium carbonate" (GCC) preferably is selected from calcium carbonate containing minerals selected from the group comprising marble, chalk, limestone and mixtures thereof. Natural ground calcium carbonate may comprise further naturally occurring components such as magnesium carbonate, alumino silicate etc.

In general, the grinding of natural ground calcium carbonate may be a dry or wet grinding step and may be carried out with any conventional grinding device, for example, under conditions such that comminution predominantly results from impacts with a secondary body, i.e. in one or more of: a ball mill, a rod mill, a vibrating mill, a roll crusher, a centrifugal impact mill, a vertical bead mill, an attrition mill, a pin mill, a hammer mill, a pulveriser, a shredder, a de-clumper, a knife cutter, or other such equipment known to the skilled man. In case the calcium carbonate containing mineral material comprises a wet ground calcium carbonate containing mineral material, the grinding step may be performed under conditions such that autogenous grinding takes place and/or by horizontal ball milling, and/or other such processes known to the skilled man. The wet processed ground calcium carbonate containing mineral material thus obtained may be washed and dewatered by well-known processes, e.g. by flocculation, filtration or forced evaporation prior to drying. The subsequent step of drying (if necessary) may be carried out in a single step such as spray drying, or in at least two steps. It is also common that such a mineral material undergoes a beneficiation step (such as a flotation, bleaching or magnetic separation step) to remove impurities.

"Precipitated calcium carbonate" (PCC) in the meaning of the present invention is a synthesized material, generally obtained by precipitation following reaction of carbon dioxide and calcium hydroxide in an aqueous environment or by precipitation of calcium and carbonate ions, for example $CaCl_2$ and $Na_2CO_3$, out of solution. Further possible ways of producing PCC are the lime soda process, or the Solvay process in which PCC is a by-product of ammonia production. Precipitated calcium carbonate exists in three primary crystalline forms: calcite, aragonite and vaterite, and there are many different polymorphs (crystal habits) for each of these crystalline forms. Calcite has a trigonal structure with typical crystal habits such as scalenohedral (S-PCC), rhombohedral (R-PCC), hexagonal prismatic, pinacoidal, colloidal (C-PCC), cubic, and prismatic (P-PCC). Aragonite is an orthorhombic structure with typical crystal habits of twinned hexagonal prismatic crystals, as well as a diverse assortment of thin elongated prismatic, curved bladed, steep pyramidal, chisel shaped crystals, branching tree, and coral or worm-like form. Vaterite belongs to the hexagonal crystal system. The obtained PCC slurry can be mechanically dewatered and dried.

According to one embodiment of the present invention, the precipitated calcium carbonate is precipitated calcium carbonate, preferably comprising aragonitic, vateritic or calcitic mineralogical crystal forms or mixtures thereof.

Precipitated calcium carbonate may be ground prior to the treatment with carbon dioxide and at least one $H_3O^+$ ion donor by the same means as used for grinding natural calcium carbonate as described above.

According to one embodiment of the present invention, the natural ground calcium carbonate or precipitated calcium carbonate is in form of particles having a weight median particle size $d_{50}$ of 0.05 to 10.0 μm, preferably 0.2 to 5.0 μm, and most preferably 0.4 to 3.0 μm. According to a further embodiment of the present invention, the natural ground calcium carbonate or precipitated calcium carbonate is in form of particles having a weight top cut particle size $d_{98}$ of 0.15 to 30 μm, preferably 0.6 to 15 μm, more preferably 1.2 to 10 μm, most preferably 1.5 to 4 μm, especially 1.6 μm.

The natural ground calcium carbonate and/or precipitated calcium carbonate may be used dry or suspended in water. Preferably, a corresponding slurry has a content of natural ground calcium carbonate or precipitated calcium carbonate within the range of 1 wt.-% to 90 wt.-%, more preferably 3 wt.-% to 60 wt.-%, even more preferably 5 wt.-% to 40 wt.-%, and most preferably 10 wt.-% to 25 wt.-% based on the weight of the slurry.

The one or more $H_3O^+$ ion donor used for the preparation of surface-reacted calcium carbonate may be any strong acid, medium-strong acid, or weak acid, or mixtures thereof, generating $H_3O^+$ ions under the preparation conditions. According to the present invention, the at least one $H_3O^+$ ion donor can also be an acid salt, generating $H_3O^+$ ions under the preparation conditions.

According to one embodiment, the at least one $H_3O^+$ ion donor is a strong acid having a $pK_a$ of 0 or less at 20° C.

According to another embodiment, the at least one $H_3O^+$ ion donor is a medium-strong acid having a $pK_a$ value from 0 to 2.5 at 20° C. If the $pK_a$ at 20° C. is 0 or less, the acid is preferably selected from sulphuric acid, hydrochloric acid, or mixtures thereof. If the $pK_a$ at 20° C. is from 0 to 2.5, the $H_3O^+$ ion donor is preferably selected from $H_2SO_3$, $H_3PO_4$, oxalic acid, or mixtures thereof. The at least one $H_3O^+$ ion donor can also be an acid salt, for example, $HSO_4^-$ or $H_2PO_4^-$, being at least partially neutralized by a corresponding cation such as $Li^+$, $Na^+$ or $K^+$, or $HPO_4^{2-}$, being at least partially neutralised by a corresponding cation such as $Li^+$, $Na^+$, $K^+$, $Mg^{2+}$ or $Ca^{2+}$. The at least one $H_3O^+$ ion donor can also be a mixture of one or more acids and one or more acid salts.

According to still another embodiment, the at least one $H_3O^+$ ion donor is a weak acid having a $pK_a$ value of greater than 2.5 and less than or equal to 7, when measured at 20° C., associated with the ionisation of the first available hydrogen, and having a corresponding anion, which is capable of forming water-soluble calcium salts. Subsequently, at least one water-soluble salt, which in the case of a hydrogen-containing salt has a $pK_a$ of greater than 7, when measured at 20° C., associated with the ionisation of the first available hydrogen, and the salt anion of which is capable of forming water-insoluble calcium salts, is additionally provided. According to the preferred embodiment, the weak acid has a $pK_a$ value from greater than 2.5 to 5 at 20° C., and more preferably the weak acid is selected from the group consisting of acetic acid, formic acid, propanoic acid, and mixtures thereof. Exemplary cations of said water-soluble salt are selected from the group consisting of potassium, sodium, lithium and mixtures thereof. In a more preferred embodiment, said cation is sodium or potassium. Exemplary anions of said water-soluble salt are selected from the group consisting of phosphate, dihydrogen phosphate, monohydrogen phosphate, oxalate, silicate, mixtures thereof and hydrates thereof. In a more preferred embodiment, said anion is selected from the group consisting of phosphate, dihydrogen phosphate, monohydrogen phosphate, mixtures thereof and hydrates thereof. In a most preferred embodiment, said anion is selected from the group consisting of dihydrogen phosphate, monohydrogen phosphate, mixtures thereof and hydrates thereof. Water-soluble salt addition may be performed dropwise or in one step. In the case of drop wise addition, this addition preferably takes place within a time period of 10 minutes. It is more preferred to add said salt in one step.

According to one embodiment of the present invention, the at least one $H_3O^+$ ion donor is selected from the group consisting of hydrochloric acid, sulphuric acid, sulphurous acid, phosphoric acid, citric acid, oxalic acid, acetic acid, formic acid, and mixtures thereof. Preferably the at least one $H_3O^+$ ion donor is selected from the group consisting of hydrochloric acid, sulphuric acid, sulphurous acid, phosphoric acid, oxalic acid, $H_2PO_4^-$, being at least partially neutralised by a corresponding cation such as $Li^+$, $Na^+$ or $K^+$, $HPO_4^{2-}$, being at least partially neutralised by a corresponding cation such as $Li^+$, $Na^+$, $K^+$, $Mg^{2+}$, or $Ca^{2+}$ and mixtures thereof, more preferably the at least one acid is selected from the group consisting of hydrochloric acid, sulphuric acid, sulphurous acid, phosphoric acid, oxalic acid, or mixtures thereof, and most preferably, the at least one $H_3O^+$ ion donor is phosphoric acid.

The one or more $H_3O^+$ ion donor can be added to the suspension as a concentrated solution or a more diluted solution. Preferably, the molar ratio of the $H_3O^+$ ion donor to the natural or precipitated calcium carbonate is from 0.01 to 4, more preferably from 0.02 to 2, even more preferably 0.05 to 1 and most preferably 0.1 to 0.58.

As an alternative, it is also possible to add the $H_3O^+$ ion donor to the water before the natural or precipitated calcium carbonate is suspended.

In a next step, the natural ground calcium carbonate or precipitated calcium carbonate is treated with carbon dioxide. If a strong acid such as sulphuric acid or hydrochloric acid is used for the $H_3O^+$ ion donor treatment of the natural ground calcium carbonate or precipitated calcium carbonate, the carbon dioxide is automatically formed. Alternatively or additionally, the carbon dioxide can be supplied from an external source.

$H_3O^+$ ion donor treatment and treatment with carbon dioxide can be carried out simultaneously which is the case when a strong or medium-strong acid is used. It is also possible to carry out $H_3O^+$ ion donor treatment first, e.g. with a medium strong acid having a $pK_a$ in the range of 0 to 2.5 at 20° C., wherein carbon dioxide is formed in situ, and thus, the carbon dioxide treatment will automatically be carried out simultaneously with the $H_3O^+$ ion donor treatment, followed by the additional treatment with carbon dioxide supplied from an external source.

Preferably, the concentration of gaseous carbon dioxide in the suspension is, in terms of volume, such that the ratio (volume of suspension):(volume of gaseous $CO_2$) is from 1:0.05 to 1:20, even more preferably 1:0.05 to 1:5.

In a preferred embodiment, the $H_3O^+$ ion donor treatment step and/or the carbon dioxide treatment step are repeated at least once, more preferably several times. According to one embodiment, the at least one $H_3O^+$ ion donor is added over a time period of at least about 5 min, typically from about 5 to about 30 min. Alternatively, the at least one $H_3O^+$ ion donor is added over a time period of about 30 min, preferably about 45 min, and sometimes about 1 h or more.

Subsequent to the $H_3O^+$ ion donor treatment and carbon dioxide treatment, the pH of the aqueous suspension, measured at 20° C., naturally reaches a value of greater than 6.0, preferably greater than 6.5, more preferably greater than 7.0, even more preferably greater than 7.5, thereby preparing the surface-reacted natural or precipitated calcium carbonate as an aqueous suspension having a pH of greater than 6.0, preferably greater than 6.5, more preferably greater than 7.0, even more preferably greater than 7.5.

It is appreciated that the $H_3O^+$ ion donor treatment and treatment with carbon dioxide can be carried over a wide temperature range. Preferably, the $H_3O^+$ ion donor treatment and treatment with carbon dioxide can be carried out at room temperature or elevated temperature. For example, if the $H_3O^+$ ion donor treatment and treatment with carbon dioxide is carried out at elevated temperature, the treatment is preferably in a range from 30 to 90° C., more preferably from 40 to 80° C. and most preferably from 50 to 80° C., such as from 60 to 80° C.

Further details about the preparation of the surface-reacted natural calcium carbonate are disclosed in WO 00/39222 A1, WO 2004/083316 A1, WO 2005/121257 A2, WO 2009/074492 A1, EP 2 264 108 A1, EP 2 264 109 A1 and US 2004/0020410 A1, the content of these references herewith being included in the present application.

Similarly, surface-reacted precipitated calcium carbonate is obtained. As can be taken in detail from WO 2009/074492 A1, surface-reacted precipitated calcium carbonate is obtained by contacting precipitated calcium carbonate with $H_3O^+$ ions and with anions being solubilized in an aqueous medium and being capable of forming water-insoluble calcium salts, in an aqueous medium to form a slurry of surface-reacted precipitated calcium carbonate, wherein said surface-reacted precipitated calcium carbonate comprises an insoluble, at least partially crystalline calcium salt of said anion formed on the surface of at least part of the precipitated calcium carbonate.

Said solubilized calcium ions correspond to an excess of solubilized calcium ions relative to the solubilized calcium ions naturally generated on dissolution of precipitated calcium carbonate by $H_3O^+$ ions, where said $H_3O^+$ ions are provided solely in the form of a counterion to the anion, i.e. via the addition of the anion in the form of an acid or non-calcium acid salt, and in absence of any further calcium ion or calcium ion generating source.

Said excess solubilized calcium ions are preferably provided by the addition of a soluble neutral or acid calcium salt, or by the addition of an acid or a neutral or acid non-calcium salt which generates a soluble neutral or acid calcium salt in situ.

Said $H_3O^+$ ions may be provided by the addition of an acid or an acid salt of said anion, or the addition of an acid or an acid salt which simultaneously serves to provide all or part of said excess solubilized calcium ions.

In a further preferred embodiment of the preparation of the surface-reacted natural ground calcium carbonate or precipitated calcium carbonate, the natural ground calcium carbonate or precipitated calcium carbonate is reacted with the acid and/or the carbon dioxide in the presence of at least one compound selected from the group consisting of silicate, silica, aluminium hydroxide, earth alkali aluminate such as sodium or potassium aluminate, magnesium oxide, or mixtures thereof. Preferably, the at least one silicate is selected from an aluminium silicate, a calcium silicate, or an earth alkali metal silicate. These components can be added to an aqueous suspension comprising the natural ground calcium carbonate or precipitated calcium carbonate before adding the acid and/or carbon dioxide.

Alternatively, the silicate and/or silica and/or aluminium hydroxide and/or earth alkali aluminate and/or magnesium oxide component(s) can be added to the aqueous suspension of natural or precipitated calcium carbonate while the reaction of natural or precipitated calcium carbonate with an acid and carbon dioxide has already started. Further details about the preparation of the surface-reacted natural or precipitated calcium carbonate in the presence of at least one silicate and/or silica and/or aluminium hydroxide and/or earth alkali aluminate component(s) are disclosed in WO 2004/083316 A1, the content of this reference herewith being included in the present application.

The surface-reacted calcium carbonate can be kept in suspension, optionally further stabilised by a dispersant. Conventional dispersants known to the skilled person can be used. A preferred dispersant is comprised of polyacrylic acids and/or carboxymethylcelluloses.

Alternatively, the aqueous suspension described above can be dried, thereby obtaining the solid (i.e. dry or containing as little water that it is not in a fluid form) surface-reacted natural ground calcium carbonate or precipitated calcium carbonate in the form of granules or a powder.

The surface-reacted calcium carbonate may have different particle shapes, such as e.g. the shape of roses, golf balls and/or brains.

According to one embodiment, the surface-reacted calcium carbonate has a specific surface area of from 15 $m^2/g$ to 200 $m^2/g$, preferably from 20 $m^2/g$ to 180 $m^2/g$, and most preferably from 25 $m^2/g$ to 160 $m^2/g$, measured using nitrogen and the BET method. The BET specific surface area in the meaning of the present invention is defined as the surface area of the particles divided by the mass of the particles. As used therein the specific surface area is measured by adsorption using the BET isotherm (ISO 9277: 2010) and is specified in $m^2/g$.

It is a requirement of the present invention that the surface-reacted calcium carbonate has a volume median particle size $d_{50}$ from 0.1 to 90 μm. According to one embodiment the surface-reacted calcium carbonate has a volume median particle size $d_{50}$ from 0.1 to 75 μm, preferably from 0.5 to 50 μm, more preferably from 1 to 40 μm, even more preferably from 1.2 to 30 μm, and most preferably from 1.5 to 15 μm.

It may furthermore be preferred that the surface-reacted calcium carbonate particles have a volume top cut particle size $d_{98}$ of from 2 to 150 μm, preferably from 4 to 100 μm, more preferably 6 to 80 μm, even more preferably from 8 to 60 μm, and most preferably from 8 to 30 μm.

The value $d_x$ represents the diameter relative to which x % of the particles have diameters less than $d_x$. This means that the $d_{98}$ value is the particle size at which 98% of all particles are smaller. The $d_{98}$ value is also designated as "top cut". The $d_x$ values may be given in volume or weight percent. The $d_{50}$ (wt) value is thus the weight median particle size, i.e. 50 wt.-% of all grains are smaller than this particle size, and the $d_{50}$ (vol) value is the volume median particle size, i.e. 50 vol. % of all grains are smaller than this particle size.

Volume median grain diameter $d_{50}$ was evaluated using a Malvern Mastersizer 2000 Laser Diffraction System. The $d_{50}$ or $d_{98}$ value, measured using a Malvern Mastersizer 2000 Laser Diffraction System, indicates a diameter value such that 50% or 98% by volume, respectively, of the particles have a diameter of less than this value. The raw data obtained by the measurement are analysed using the Mie theory, with a particle refractive index of 1.57 and an absorption index of 0.005.

The weight median grain diameter is determined by the sedimentation method, which is an analysis of sedimentation behaviour in a gravimetric field. The measurement is made with a Sedigraph™ 5100 or 5120, Micromeritics Instrument Corporation. The method and the instrument are known to the skilled person and are commonly used to determine grain size of fillers and pigments. The measurement is carried out in an aqueous solution of 0.1 wt.-% $Na_4P_2O_7$. The samples were dispersed using a high speed stirrer and sonicated.

The processes and instruments are known to the skilled person and are commonly used to determine grain size of fillers and pigments.

The specific pore volume is measured using a mercury intrusion porosimetry measurement using a Micromeritics Autopore V 9620 mercury porosimeter having a maximum applied pressure of mercury 414 MPa (60 000 psi), equivalent to a Laplace throat diameter of 0.004 μm (~nm). The equilibration time used at each pressure step is 20 seconds. The sample material is sealed in a 5 $cm^3$ chamber powder penetrometer for analysis. The data are corrected for mercury compression, penetrometer expansion and sample material compression using the software Pore-Comp (Gane, P. A. C., Kettle, J. P., Matthews, G. P. and Ridgway, C. J., "Void Space Structure of Compressible Polymer Spheres and Consolidated Calcium Carbonate Paper-Coating Formulations", Industrial and Engineering Chemistry Research, 35(5), 1996, p. 1753-1764).

The total pore volume seen in the cumulative intrusion data can be separated into two regions with the intrusion data from 214 μm down to about 1-4 μm showing the coarse packing of the sample between any agglomerate structures contributing strongly. Below these diameters lies the fine interparticle packing of the particles themselves. If they also have intraparticle pores, then this region appears bi-modal, and by taking the specific pore volume intruded by mercury into pores finer than the modal turning point, i.e. finer than the bi-modal point of inflection, the specific intraparticle pore volume is defined. The sum of these three regions gives the total overall pore volume of the powder, but depends strongly on the original sample compaction/settling of the powder at the coarse pore end of the distribution.

By taking the first derivative of the cumulative intrusion curve the pore size distributions based on equivalent Laplace diameter, inevitably including pore-shielding, are revealed. The differential curves clearly show the coarse agglomerate pore structure region, the interparticle pore region and the intraparticle pore region, if present. Knowing the intraparticle pore diameter range it is possible to subtract the remainder interparticle and interagglomerate pore volume from the total pore volume to deliver the desired pore volume of the internal pores alone in terms of the pore volume per unit mass (specific pore volume). The same principle of subtraction, of course, applies for isolating any of the other pore size regions of interest.

Preferably, the surface-reacted calcium carbonate has an intra-particle intruded specific pore volume in the range from 0.1 to 2.3 $cm^3/g$, more preferably from 0.2 to 2.0 $cm^3/g$, especially preferably from 0.4 to 1.8 $cm^3/g$ and most preferably from 0.6 to 1.6 $cm^3/g$, calculated from mercury porosimetry measurement.

The intra-particle pore size of the surface-reacted calcium carbonate preferably is in a range of from 0.004 to 1.6 μm, more preferably in a range of between 0.005 to 1.3 μm, especially preferably from 0.006 to 1.15 μm and most preferably of 0.007 to 1.0 μm, e.g. 0.004 to 0.16 μm determined by mercury porosimetry measurement.

According to an exemplary embodiment, the surface-reacted calcium carbonate has a volume median particle size $d_{50}$ from 1.5 to 15 μm, preferably from 4 to 6 μm; a specific surface-area of from 30 to 140 $m^2/g$, preferably from 60 to 100 $m^2/g$, measured using nitrogen and the BET method; and an intra-particle intruded specific pore volume from 0.2 to 2.0 $cm^3/g$, preferably from 0.6 to 1.6 $cm^3/g$, calculated from mercury porosimetry measurement.

Due to the intra and interpore structure of the surface-reacted calcium carbonate, it can be a superior agent to deliver previously adsorbed and/or absorbed materials over time relative to common materials having similar specific surface areas. Thus, generally, any agent fitting into the intra- and/or inter particle pores of the surface-reacted calcium carbonate is suitable to be transported by the surface-reacted calcium carbonate according to the invention. For example, active agents such as those selected from the group comprising pharmaceutically active agents, biologically active agents, disinfecting agents, preservatives, flavouring agents, surfactants, oils, fragrances, essential oils, and mixtures thereof can be used. According to one embodiment, at least one active agent is associated with the surface-reacted calcium carbonate.

According to one embodiment of the present invention, the surface-reacted calcium carbonate comprises an water-insoluble, at least partially crystalline calcium salt of an anion of the at least one acid, which is formed on the surface of the natural ground calcium carbonate or precipitated calcium carbonate. According to one embodiment, the water-insoluble, at least partially crystalline salt of an anion of the at least one acid covers the surface of the natural ground calcium carbonate or precipitated calcium carbonate at least partially, preferably completely. Depending on the employed at least one acid, the anion may be sulphate, sulphite, phosphate, citrate, oxalate, acetate, formiate and/or chloride.

For example, the use of phosphoric acid, $H_2PO_4^-$ or $HPO_4^{2-}$ as the $H_3O^+$ ion donor may lead to the formation of hydroxylapatite. Therefore, in a preferred embodiment, the at least one water-insoluble calcium salt is hydroxylapatite.

According to one embodiment, the at least one water-insoluble calcium salt is hydroxylapatite, wherein the surface-reacted calcium carbonate provides a ratio of hydroxylapatite to calcite, aragonite and/or vaterite, preferably to calcite, in the range of from 1:99 to 99:1 by weight. Preferably, the surface-reacted calcium carbonate may provide a ratio of hydroxylapatite to calcite, aragonite and/or vaterite, preferably to calcite, in the range of from 1:9 to 9:1, preferably 1:7 to 8:1, more preferably 1:5 to 7:1 and most preferably 1:4 to 7:1 by weight.

In a similar manner, the use of other $H_3O^+$ ion donors may lead to the formation of corresponding water-insoluble calcium salts other than calcium carbonate on at least part of the surface of the surface-reacted calcium carbonate. In one embodiment, the at least one water-insoluble calcium salt is thus selected from the group consisting of octacalcium phosphate, hydroxylapatite, chlorapatite, fluorapatite, carbonate apatite and mixtures thereof, wherein the surface-reacted calcium carbonate shows a ratio of the at least one water-insoluble calcium salt to calcite, aragonite and/or vaterite, preferably to calcite, in the range of from 1:99 to 99:1, preferably from 1:9 to 9:1, more preferably from 1:7 to 8:1, even more preferably from 1:5 to 7:1 and most preferably from 1:4 to 7:1 by weight.

According to one embodiment the surface-reacted calcium carbonate comprises:
(i) a specific surface area of from 15 to 200 $m^2/g$ measured using nitrogen and the BET method according to ISO 9277:2010, and
(ii) an intra-particle intruded specific pore volume in the range of from 0.1 to 2.3 $cm^3/g$ calculated from mercury porosimetry measurement.

In one embodiment of the present invention, the surface-reacted calcium carbonate as described herein is provided in the form of granules. "Granules" in the meaning of the present invention are agglomerates of the surface-reacted calcium carbonate and have a particle size of 20 to 300 μm. That is to say, the granules having a particle size of 20 to 300 μm comprise primary particles of the surface-reacted calcium carbonate having a volume median particle size $d_{50}$ from 0.1 to 90 μm.

The Cosmetic and/or Skin Care Composition

The invention refers to the use of surface-reacted calcium carbonate as defined herein as skin appearance modifier in a cosmetic and/or skin care composition.

It was surprisingly found by the inventors that the use of surface-reacted calcium carbonate as defined herein in a cosmetic and/or skin care composition leads to an improved skin appearance modification of such compositions compared to the use of other skin appearance modifier.

For example, it was found that the use of surface-reacted calcium carbonate as defined herein in a cosmetic and/or skin care composition leads to an improved covering power of such composition compared to the use of other covering agents, and especially compared to ground calcium carbonate. Furthermore, the inventors found that a cosmetic and/or skin care composition comprising a surface-reacted calcium carbonate according to the present invention is more effective in covering the skin surface than a similar composition not containing the surface-reacted calcium carbonate. Based thereon, the cosmetic and/or skin care composition is more effective in concealing wrinkles or hiding skin imperfections.

It was also found that that the use of the surface-reacted calcium carbonate as defined herein in a cosmetic and/or skin care composition leads to a decreased gloss or shininess of the skin surface, and therefore has the effect of a mattifying agent.

Without wishing to be bound by theory, the decreased gloss or shininess of the skin surface might be due to a decrease in sebum rate. The decrease in sebum rate is another surprising effect of the use of surface-reacted calcium carbonate as defined herein in a cosmetic and/or skin care composition.

Furthermore, the inventors found that the surface-reacted calcium carbonate leads to an improved skin appearance modification in combination with an improved skin feel modification.

According to one embodiment, the skin appearance modifier is a covering agent, a mattifying agent and/or a skin colour modifier, and preferably a covering agent and/or a mattifying agent. In one embodiment, the skin appearance modifier is a covering agent and/or a mattifying agent and further provides skin feel modification.

It is appreciated that the amount of the surface-reacted calcium carbonate in the cosmetic and/or skin care composition may vary in a wide range and may be dependent on the cosmetic and/or skin care composition to be prepared and/or the manufacturer's needs and/or legal requirements. For example, in case a skin care and/or cosmetic composition in form of e.g. a paste or an emulsion is prepared, the amount of the surface-reacted calcium carbonate may be below 50 wt.-%, based on the total weight of the cosmetic and/or skin care composition. On the other hand, in case a skin care and/or cosmetic composition in form of e.g. a powder is prepared, the amount of surface-reacted calcium carbonate may be above 50 wt.-%, based on the total weight of the cosmetic and/or skin care composition.

In general, the surface-reacted calcium carbonate can thus be present in the cosmetic and/or skin care composition in an amount from 0.1 to 90 wt.-%, based on the total weight of the cosmetic and/or skin care composition, and preferably from 0.5 to 80 wt.-%.

According to one embodiment of the present invention, the surface-reacted calcium carbonate is present in the cosmetic and/or skin care composition in an amount from 0.1 to 50 wt.-%, based on the total weight of the cosmetic and/or skin care composition, preferably from 0.5 to 20 wt.-%, more preferably from 1 to 10 wt.-%, and most preferably from 3 to 10 wt.-%.

In an alternative embodiment of the present invention, the surface-reacted calcium carbonate is present in the cosmetic and/or skin care composition in an amount from 50 to 90 wt.-%, based on the total weight of the cosmetic and/or skin care composition, and preferably from 60 to 80 wt.-%.

In case the cosmetic and/or skin care composition is prepared in form of a paste or an emulsion, i.e. not in form of a powder, the pH value of the composition may be adjusted to any value suitable for a cosmetic and/or skin care composition. Thus, the cosmetic and/or skin care composition as described herein is not limited to a specific pH value.

The inventors surprisingly found that the pH value of the cosmetic composition comprising the surface-reacted calcium carbonate according to the invention can be adjusted to a value of ≤7.5, and can even be adjusted to a pH value from 4.0 to 7.0 without showing a negative impact on the stability of the calcium carbonate particles. Usually cosmetic compositions containing, for example, ground calcium carbonate tend to become unstable when the pH value is adjusted below 7.05, and especially below 7.0, due to the liberation of carbon dioxide from the carbonate in the acidic medium. Thus, the cosmetic and/or skin care composition comprising the surface-reacted calcium carbonate has an improved acid resistance compared to prior art cosmetic products containing, for example, ground calcium carbonate which has not been surface-reacted as described above. This is particularly advantageous since cosmetic and/or skin care products are usually formulated to have a preferred pH value of below 7.5, or of below 7.0 in order to approach or match the natural pH level of the skin. Without wishing to be bound by theory, the inventors speculate that the surface treatment of the calcium carbonate as defined herein leads to a specific surface structure which exhibits an improved acid resistance compared to a calcium carbonate being not surface-reacted.

The cosmetic and/or skin care composition is however not limited to a pH value of ≤7.5, and may also be adjusted to a pH value of ≤8.5.

The cosmetic and/or skin care composition preferably has a pH value of ≤8.5, preferably ≤8.0, more preferably ≤7.0 and most preferably from 4.0 to 7.0. The cosmetic and/or skin care composition may further comprise water and/or at least one oil. Thus, according to one embodiment of the present invention, the cosmetic and/or skin care composition further comprises water. According to another embodiment, the cosmetic and/or skin care composition further comprises at least one oil. According to a preferred embodiment, the cosmetic and/or skin care composition further comprises water and at least one oil. An "oil" in the meaning of the present invention is a liquid or solid silicon- and/or hydrocarbon-containing compound.

The water may be selected from tap water, distilled water, deionized water, or mixtures thereof, and preferably is deionized water.

The at least one oil may be selected from any oil which is suitable to be used in cosmetic and/or skin care compositions. Oils which are suitable for use in cosmetic and/or skin care compositions are known to the skilled person and are described in, for example, Regulation EC No 1223/2009 of the European Parliament and of the Council of 30 Nov. 2009, and must not form part of the list of prohibited substances disclosed therein.

According to one embodiment of the present invention, the at least one oil is selected from the group consisting of vegetable oils and esters thereof, alkane coconut ester, plant extracts, animal fats, siloxanes, fatty acids and esters thereof, petrolatum, glycerides and pegylated derivatives thereof, and mixtures thereof.

For example, a suitable vegetable oil may be palm oil, soybean oil, rapeseed oil, sunflower seed oil, peanut oil, cottonseed oil, palm kernel oil, coconut oil, olive oil, jojoba oil, corn oil, jumbú oil, guava oil, grape seed oi, hazelnut oil, linseed oil, rice bran oil, safflower oil, sesame oil, acai palm oil, graviola oil, tucuma oil, brazil oil, carapa oil, buriti oil, passion fruit oil or pracaxi oil.

Suitable plant extracts may be prepared, for example, from *Castanea Sativa, Prunus Dulcis, Juglans Regia* L., *Olea Europaea, Helichrysum stoechas, Quercus Robur, Glycyrrhiza Glabra, Vitis Vinifera, Crataegus Monogyna Jacq*, or *Pinus Pinaster.*

Suitable animal fats can be obtained, for example, from tallow.

Suitable siloxanes are, for example, dimethicone, cetyl dimethicone, dimethiconol, detearyl methicone, cyclopentasiloxane, cyclomethicone, stearyl dimethicone, trimethylsilylamodimethicone, stearoxy dimethicone, amodimethicone, behenoxy dimethicone, dimethicone copolyol, polysiloxane, laurylmethicone copolyol or cetyl dimethicone copolyol.

Suitable fatty acids are, for example, palmitic acid, stearic acid, myristic acid, oleic acid, palmitoleic acid, linoleic acid, linolenic acid, capric acid, caprylic acid, arachidonic acid and esters thereof.

Suitable petrolatum may be any petrolatum with a refined grade approved for cosmetic use, and preferably has a melting point between 35° C. and 70° C.

Suitable glycerides are, for example, mono-, di, or triglycerides from palmitic acid, stearic acid, myristic acid, oleic acid, palmitoleic acid, linoleic acid, linolenic acid, capric acid, caprylic acid, and mixtures thereof.

In one embodiment, the at least one oil comprises, preferably consists of, one oil. Alternatively, the at least one oil comprises, preferably consists of, two or more oils. For example, the at least one oil comprises, preferably consists of, two or three oils. Preferably, the at least one oil comprises, preferably consists of, two or more oils.

It is appreciated that the cosmetic and/or skin care composition may comprise the water and/or the at least one oil and their amounts in dependence of the cosmetic and/or skin care composition to be prepared and/or the manufacturer's needs. According to one embodiment, the water is present in an amount of from 1 to 95 wt.-%, preferably from 15 to 90 wt.-%, more preferably from 25 to 80 wt.-%, even more preferably from 35 to 75 wt.-%, and most preferably from 45 to 65 wt.-%, based on the total weight of the cosmetic and/or skin care composition. According to another embodiment, the at least one oil is present in an amount of from 1 to 95 wt.-%, preferably from 2 to 75 wt.-%, more preferably from 5 to 55 wt.-%, even more preferably from 7.5 to 35 wt.-%, and most preferably from 10 to 20 wt.-%, based on the total weight of the cosmetic and/or skin care composition.

In case the cosmetic and/or skin care composition comprises water and at least one oil, the composition may be a water-based dispersion or an oil-based dispersion. Thus, according to one embodiment, the cosmetic and/or skin care composition is a water-based dispersion. According to another embodiment, the composition is an oil-based dispersion. According to a preferred embodiment, the cosmetic and/or skin care composition is a water-based dispersion. A "water-based dispersion" in the meaning of the present invention refers to a composition wherein water forms a continuous phase and the oil a dispersed phase, i.e. the oil is dispersed in the continuous water phase. An "oil-based dispersion" in the meaning of the present invention refers to a composition wherein oil forms a continuous phase and water a dispersed phase, i.e. water is dispersed in the continuous water phase. According to yet another embodiment, the water is present in an amount of from 1 to 95 wt.-%, preferably from 15 to 90 wt.-%, more preferably from 25 to 80 wt.-%, even more preferably from 35 to 75 wt.-%, and most preferably from 45 to 65 wt.-%, and the at least one oil is present in an amount of from 1 to 95 wt.-%, preferably from 2 to 75 wt.-%, more preferably from 5 to 55 wt.-%, even more preferably from 7.5 to 35 wt.-%, and most preferably from 10 to 20 wt.-%, based on the total weight of the cosmetic and/or skin care composition.

As described above, the intra and interpore structure of the surface-reacted calcium carbonate can make it a superior agent to deliver previously adsorbed and/or absorbed materials over time relative to common materials having similar specific surface areas. Thus, generally, any agent fitting into the intra- and/or inter particle pores of the surface-reacted calcium carbonate is suitable to be transported by the surface-reacted calcium carbonate according to the invention. Accordingly, it is possible that the cosmetic and/or skin care composition comprises at least one active agent being adsorbed onto and/or absorbed into the surface of the surface-reacted calcium carbonate. According to one embodiment of the present invention, the cosmetic and/or skin care composition comprises at least one active agent being adsorbed onto and/or absorbed into the surface of the surface-reacted calcium carbonate.

The inventors surprisingly found that a cosmetic and/or skin care composition comprising an active agent being adsorbed onto and/or absorbed into the surface of the surface-reacted calcium carbonate has advantageous effects for the user. For example, it has been found that an active agent such as an essential and/or scented oil being adsorbed onto and/or absorbed into the surface of the surface-reacted calcium carbonate can positively influence the skin feeling of the user during or after application of the cosmetic and/or skin care composition by providing a fresh sensation or a particularly pleasant scent.

According to a preferred embodiment of the present invention, the at least one active agent is selected from pharmaceutically active agents, biologically active agents, vitamins, disinfecting agents, preservatives, flavouring agents, surfactants, oils, fragrances, essential oils such as limonene or mint oil, and mixtures thereof, and preferably biologically active agents, scented oils and essential oils. Preferably, the at least one active agent is an essential oil. More preferably, the at least one active agent is mint oil. "Mint oil" in the meaning of the present invention is an oil that is obtained from wild mint *M. Arvensis* and typically comprises a variety of different terpeneoids and/or terpenes such as menthol, isomenthone, menthone, menthylacetate, limonene, α-pinene and β-pinene. Menthol is usually the major component of mint oil.

The at least one active agent may be adsorbed onto and/or absorbed into the surface of the surface-reacted calcium carbonate in specific amounts. According to one embodiment of the present invention, the amount of the at least one agent being adsorbed onto and/or absorbed into the surface of the surface-reacted calcium carbonate ranges from 0.1 to 99 wt.-%, based on the weight of the surface-reacted calcium carbonate, preferably ranges from 30 to 95 wt.-%, more preferably from 50 to 90 wt.-%, and most preferably from 70 to 85 wt.-%.

The cosmetic and/or skin care composition may also comprise further additives. Additives that are suitable for cosmetic compositions are known to the skilled person and are described in, for example, Regulation EC No 1223/2009 of the European Parliament and of the Council of 30 Nov. 2009, and must not form part of the list of prohibited substances disclosed therein. According to one embodiment of the present invention, the cosmetic and/or skin care composition further comprises at least one additive selected from the group consisting of bleaching agents, thickeners, stabilizers, chelating agents, preserving agents, wetting agents, emulsifiers, emollients, fragrances, colorants, skin tanning compounds, antioxidants, minerals, pigments, UV-A and/or UV-B filter, and mixtures thereof.

For example, the emulsifier can be an ionic emulsifier, more preferably and anionic or cationic emulsifier. The emulsifier can be of natural vegetable origin e.g. polyglycerol ester or synthetic. More preferably, the emulsifier may be selected from the group comprising PEG compounds, PEG-free emulsifier, silicone-based emulsifier, silicones, waxes and mixtures thereof. For example, the emulsifier may be selected from the group comprising PEG compounds such as PEG-8 myristate, PEG-30 glyceryl cocoate, PEG-80 glyceryl cocoate, PEG-15 soyamide/IPDI copolymer, PEG-40 sorbitan peroleate, PEG-150 stearate and mixtures thereof, carbomer, carboxymethylcellulose, ceresin (aka mineral wax), diethanolamine (DEA), isopropyl stearate, isopropyl laurate, isopropyl palmitate, isopropyl oleate, polysorbate 20, polysorbate 60, polysorbate 80, propylene glycol, sorbitan stearate, sorbitan laurate, sorbitan palmitate, sorbitan oleate, steareth-20, triethanolamine (TEA), beeswax, candelilla wax, carnauba wax, cetearyl alcohol, cetearyl wheat bran glycosides, cetearyl wheat straw glycosides, decyl glucoside, jojoba, lecithin, vegetable glycerin, xanthan gum, coco glucoside, coconut alcohol, arachidyl alcohol, behenyl alcohol, arachidyl glucoside, and mixtures thereof.

The fragrance may be selected from a natural and/or synthetic fragrance known as being suitable in cosmetic formulations.

The colorant may be selected from a natural and/or synthetic colorant, pigment or dye such as $Fe_2O_3$, ZnO, $TiO_2$, mica, talc, bismuth oxychloride, and mixtures thereof.

According to one embodiment, the skin tanning compound is preferably dihydroxyacetone (DHA) and/or erythrulose. For example, the skin tanning compound may be dihydroxyacetone (DHA) or erythrulose. Alternatively, the skin tanning compound may be dihydroxyacetone (DHA) in combination with erythrulose.

According to one embodiment, the cosmetic and/or skin care composition further comprises at least one emollient. Examples of suitable emollients are isocetylstearoylstearate, ethylhexyl stearate, octyldodecyl stearoyl stearate, isocetyl stearate, isopropyl isostearate, isostearyl isostearate, ethylhexyl hydroxystearate, ethylhexyl palmitate, isopropyl palmitate, neopentyl glycol diheptanoate, ethylhexyl isononanoate, isononyl isononanoate, cetearyl isononanoate, cetearyl octanoate, diisopropyl adipate, dicapryl adipate, diisostearylmalate, decyl oleate, isodecyl oleate, diisopropyl myristate, isostearyl neopentanoate, octyl dodecyl neopentanoate, ethylhexyl cocoate, PEG-7 glyceril cocoate, C12-15 alkyl benzoate, C16-17 alkyl benzoate, stearyl benzoate, isostearyl benzoate, ethylhexyl benzoate, octyldodecyl benzoate, cocoglyceride, coconut alkanes, coco-caprylate/caprate, and mixtures thereof. For example, the cosmetic composition may further comprise a mixture of cocoglyceride, isononyl isononanoate, coconut alkanes and coco-caprylate/caprate as emollient.

Additionally or alternatively, the cosmetic and/or skin care composition further comprises at least one thickener. Examples of suitable thickener for a water-based dispersion are thickener based on silicate such as magnesium silicate, aluminium silicate and mixtures thereof, hydroxyethylcellulose, cellulose, microcrystalline cellulose, xanthan gum or polyacrylamide. Examples of suitable thickener for an oil-based dispersion are selected from the group comprising silicate such as magnesium silicate, aluminium silicate, silica dimethylsilicate, hydrophobic fumed silica, polyacrylic acid, salts of polyacrylic acid, derivatives of polyacrylic acid, PEG compounds such as PEG-8 myristate, PEG-30 glyceryl cocoate, PEG-80 glyceryl cocoate, PEG-15 soyamide/IPDI copolymer, PEG-40 sorbitan peroleate, PEG-150 stearate and mixtures thereof, methyl cellulose, ethyl cellulose, propyl cellulose, carboxymethylcellulose, xanthan gum, ammonium acryloyldimethyltaurate/VP copolymer and mixtures thereof.

Additionally or alternatively, the cosmetic and/or skin care composition further comprises at least one preserving agent. Examples of suitable preserving agents are phenoxyethanol, ethylhexylglycerin, parabens such as methyl paraben, ethyl paraben, propyl paraben, butyl paraben, isobutyl paraben and mixtures thereof, benzoic acid, sodium benzoate, sorbic acid, potassium sorbate and mixtures thereof, or plant extracts with preservative function such as rosemary extracts. For example, said mixture may comprise phenoxyethanol, methyl paraben, ethyl paraben and isobutyl paraben.

Examples of suitable chelating agents are a polyphosphate, ethylenediamine-N,N,N',N'-tetraacetic acid (EDTA), pyridine-2,6-dicarboxylic acid (DPA), diethylenetriaminepentaacetic acid (DTPA), N,N-bis(carboxymethyl)glycine (NTA), ammonium diethyldithiophosphate (DDPA), disodium ethylenediamine-tetraacetate ($Na_2H_2EDTA$), calcium-disodium-ethylenediamine-tetraacetate ($CaNa_2EDTA$), citric acid and salts of citric acid, sodium gluconate, and mixtures thereof.

Examples of suitable wetting agents are primary alcohols such as 1-ethanol, 1-propanol, 1-butanol, isobutanol 1-pentanol, isoamyl alcohol, 2-methyl-1butanol, 1-hexanol, 1-heptanol, 1-octanol, 1-nonanol, 1-decanol, 1-undecanol, 1-dodecanol, 1-tridecanol, 1-tetradecanol, 1-pentadecanol, cetyl alcohol, 1-heptadecanol, stearyl alcohol, 1-nonadecanol and mixtures thereof, secondary alcohols such as isopropanol, 2-butanol, 2-pentanol, 2-hexanol, 2-heptanol and mixtures thereof, tertiary alcohols such as tert.-butyl alcohol, tert.-amyl alcohol, 2-methyl-2-pentanol, 2-methylhexan-2-ol, 2-methylheptan-2-ol, 3-methyl-3-pentanol, 3-methyloctan-3-ol and mixtures thereof, diols such as 1,2-diols or 1,3-diols, e.g. 1,3-propandiol, urea, and mixtures thereof.

Examples of suitable antioxidants are butylhydroxyanisol (BHA), butylhydroxytoluol (BHT), gallate, carotinoid, polyphenols such as resveratrol, flavonoid and mixtures thereof, derivatives of polyphenols, ascorbic acid and salts thereof, tocopherol and salts thereof, betacarotin, ubichinon, tocotrienol, dihydroquercetin, antioxidants of natural origin, and mixtures thereof.

Examples of suitable pigments are inorganic red pigments such as iron oxide, ferric hydroxide and iron titanate, inorganic brown pigments such as γ-iron oxide, inorganic yellow pigments such as yellow iron oxide and yellow ocher, inorganic black pigments such as black iron oxide and carbon black, inorganic purple pigments such as manganese violet and cobalt violet, inorganic green pigments such as chromium hydroxide, chrome oxide, cobalt oxide and cobalt titanate, inorganic blue pigments such as iron blue and ultramarine, particulate powders such as particulate titanium oxide, particulate cerium oxide and particulate zinc oxide, laked tar dyes, laked natural dyes, and synthetic resin powders combining foregoing powders.

The bleaching agent may be selected from one or more of a vitamin B3 compound or its derivative e.g. niacin, nicotinic acid or niacinamide or other well-known bleaching agents e.g. adapalene, aloe extract, ammonium lactate, anethole derivatives, apple extract, arbutin, azelaic acid, kojic acid, bamboo extract, bearberry extract, bletilla tuber, bupleurum falcatum extract, burnet extract, butyl hydroxy anisole, butyl hydroxy toluene, citrate esters, Chuanxiong, Dang-Gui, deoxyarbutin, 1,3-diphenyl propane derivatives, 2,5-dihydroxybenzoic acid and its derivatives, 2-(4-acetoxyphenyl)-1,3-dithane, 2-(4-hydroxyphenyl)-1,3-dithane, ellagic acid, escinol, estragole derivatives, Fadeout (Pentapharm), Fangfeng, fennel extract, ganoderma extract, gaoben, Gatuline Whitening (Gattlefosse), genistic acid and its derivatives, glabridin and its derivatives, gluco pyranosyll-ascorbate, gluconic acid, glycolic acid, green tea extract, 4-hydroxy-5-methyl-3[2H]-furanone, hydroquinone, 4-hydroxyanisole and its derivatives, 4-hydroxy benzoic acid derivatives, hydroxycaprylic acid, inositol ascorbate, lemon extract, linoleic acid, magnesium ascorbyl phosphate, Melawhite (Pentapharm), moms alba extract, mulberry root extract, 5-octanoyl salicylic acid, parsley extract, phellinus linteus extract, pyrogallol derivatives, 2,4-resorcinol derivatives, 3,5-resorcinol derivatives, rose fruit extract, salicylic acid, Song-Yi extract, 3,4,5-trihydroxybenzyl derivatives, tranexamic acid, vitamins like vitamin B6, vitamin B12, vitamin C, vitamin A, dicarboxylic acids, resorcinol derivatives, extracts from plants viz. rubia and symplocos, hydroxycarboxylic acids like lactic acid and their salts e.g. sodium lactate, and mixtures thereof. Vitamin B3 compound or its derivative e.g. niacin, nicotinic acid or niacinamide are the more preferred bleaching agents, most preferred being niacinamide. Niacinamide, when used, is preferably present in an amount in the range of 0.1 to 10 wt.-%, more preferably 0.2 to 5 wt.-%, based on the total weight of the cosmetic composition.

The minerals may be selected from any minerals suitable for the use in a cosmetic and/or skin care composition. For example, the cosmetic and/or skin care composition may contain silicates such as talc, mica and/or kaolin.

UV-A and/or UV-B filter may be selected from inorganic UV filter and/or organic UV filter. Suitable inorganic UV filter are, for example, selected from the group consisting of titanium dioxide, zinc oxide, iron oxide, hydroxyapatite, cerium oxide, calcium-doped cerium oxide, cerium phosphate, and mixtures thereof. Suitable organic UV filter are, for example, selected from the group comprising cinnamic acid and its salts, derivatives of salicylic acid and its salts, benzophenones, derivatives of aminobenzoic acid and its salts, dibenzoylmethanes, benzylidenecamphor derivatives, benzimidazole derivatives, diphenylacrylate derivatives, acrylamide derivatives, benzotriazole derivatives, triazine derivatives, benzalmalonate derivatives, aminobenzoate derivatives, octocrylene, and mixtures thereof.

It is appreciated that the cosmetic composition may comprise the at least one further additive and its amount in dependence of the cosmetic composition to be prepared and/or the manufacturer's needs. For example, the cosmetic composition may comprise 0.1 to 10 wt.-% of thickeners, stabilizers, chelating agents, bleaching agents, wetting agents, emulsifiers, emollients, and/or skin tanning compounds, and/or 0.1 to 15 wt.-% of preserving agents, fragrances, colorants, antioxidants, minerals, pigments, UV-A and/or UV-B filter wherein the wt.-% is based on the total weight of the cosmetic composition.

In one embodiment, the at least one additive comprises, preferably consists of, one additive. Alternatively, the at least one additive comprises, preferably consists of, two or more additives. For example, the at least one additive comprises, preferably consists of, ten to fifteen additives. Preferably, the at least one additive comprises, preferably consists of, two or more additives.

The cosmetic and/or skin care composition may be provided in the form of any cosmetic and/or skin care product being applicable to the skin of the face and/or body. According to one embodiment of the present invention, the cosmetic and/or skin care composition is selected from an eye make-up product, a facial make-up product, a lip care product, a hand care product, a skin care product, or a combination product thereof.

Furthermore, the cosmetic and/or skin care composition may have a certain Brookfield viscosity. For the purpose of the present invention, the term "viscosity" or "Brookfield viscosity" refers to Brookfield viscosity. The Brookfield viscosity is for this purpose measured by a Brookfield (Typ RVT) viscometer at 25° C.±1° C. at 100 rpm after 30 seconds using an appropriate spindle and is specified in mPa·s. According to one embodiment of the present invention, the cosmetic and/or skin care composition has a Brookfield viscosity in a range from 4 000 to 50 000, preferably from 10 000 to 45 000, more preferably from 15 000 to 40 000, even more preferably from 20 000 to 40 000, and most preferably from 25 000 to 40 000 mPa·s at 25° C.

The use of the surface-reacted calcium carbonate as skin appearance modifier in a cosmetic and/or skin care composition may also modify the skin feeling of the user during application or shortly thereafter. Thus, according to one embodiment of the present invention, the surface-reacted calcium carbonate further provides skin feel modification.

The inventors surprisingly found that a cosmetic and/or skin care composition comprising a surface-reacted calcium carbonate provides the user with an improved skin feel during and/or after the application. In particular, the cosmetic and/or skin care composition can be easily spread on the skin and the application provides the user with a non-sticky, non-greasy and/or a soft skin feeling. Furthermore, the skin feel modification may be altered or more prominent in certain aspects, in case a surface-reacted calcium carbonate is used, wherein at least one active agent is adsorbed onto and/or absorbed into the surface of the surface-reacted calcium carbonate. Thus, by selecting a specific active agent, the skin feel modification may be further influenced. For example, in case mint oil is absorbed onto and/or absorbed into the surface of the surface-reacted calcium carbonate, the skin feel modification may additionally relate to freshness and/or a pleasant odor.

According to one embodiment, the skin feel modification relates to a reduced dry time, greasiness reduction, fluidity, spreadability, homogeneity, tack reduction, and/or resistance, and preferably greasiness reduction and/or spreadability improvement.

According to another embodiment, the skin feel modification relates to a fresh feeling, reduced dry time, greasiness reduction, fluidity, spreadability, odor, homogeneity, tack reduction, and/or resistance, and preferably greasiness reduction, spreadability improvement, odor and/or freshness.

Preparation of the Cosmetic and/or Skin Care Composition

The method for the preparation of the cosmetic and/or skin care composition comprises at least the provision of a surface-reacted calcium carbonate as skin appearance modifier. The surface-reacted calcium carbonate has a volume median particle size $d_{50}$ from 0.1 to 90 µm and is a reaction product of natural ground calcium carbonate or precipitated calcium carbonate with carbon dioxide and one or more $H_3O^+$ ion donors, wherein the carbon dioxide is formed in situ by the $H_3O^+$ ion donors treatment and/or is supplied from an external source.

The surface-reacted calcium carbonate may be provided in any suitable liquid or dry form. For example, the surface-reacted calcium carbonate may be in form of a powder and/or a suspension. The suspension can be obtained by mixing the surface-reacted calcium carbonate with a solvent, preferably water. The surface-reacted calcium carbonate to be mixed with a solvent, and preferably water, may be provided in any form, for example, as suspension, slurry, dispersion, paste, powder, a moist filter cake or in pressed or granulated form, and preferably is provided as a powder.

The term "dispersion" or "suspension" in the meaning of the present invention refers to a system comprising a dispersing medium or solvent and at least one inorganic particulate material, wherein at least a part of the particles of the at least one inorganic particulate material are present as insoluble solids or suspended particles in the dispersing medium or solvent.

The suspension can be undispersed or dispersed, i.e. the suspension includes a dispersant, and thus, forms a dispersion, e.g. an aqueous dispersion. Suitable dispersants are known in the art, and may be selected, e.g., from polyelectrolytes, polyhydroxystearic acid, acetylacetone, propylamine, oleic acid, polyacrylates, carboxymethylcellulose based dispersants, and mixtures thereof.

The solids content of the suspension, preferably aqueous suspension, of the surface-reacted calcium carbonate may be from 1 to 85 wt.-%, more preferably from 5 to 75 wt.-%, and most preferably from 10 to 40 wt.-%, based on the total weight of the suspension.

In case the surface-reacted calcium carbonate is provided in dry form, the moisture content of the surface-reacted calcium carbonate can be between 0.01 and 5 wt.-%, based on the total weight of the surface-reacted calcium carbonate. The moisture content of the surface-reacted calcium carbonate can be, for example, less than or equal to 1.0 wt.-%, based on the total weight of the surface-reacted calcium carbonate, preferably less than or equal to 0.5 wt.-%, and more preferably less than or equal to 0.2 wt.-%. According to another example, the moisture content of the surface-reacted calcium carbonate may be between 0.01 and 0.15 wt.-%, preferably between 0.02 and 0.10 wt.-%, and more preferably between 0.03 and 0.07 wt.-%, based on the total weight of the surface-reacted calcium carbonate.

The method for the preparation of the cosmetic and/or skin care composition may further comprise the provision of water and/or at least one oil and the mixing of the water and/or at least one oil with the surface-reacted calcium carbonate.

The mixing of the water and/or the at least one oil and the surface-reacted calcium carbonate may be carried out in any manner known by the skilled person. The mixing may be carried out under conventional mixing conditions. The skilled man will adapt these mixing conditions (such as the configuration of mixing pallets and mixing speed) according to his process equipment. It is appreciated that any mixing method which would be suitable to form a cosmetic and/or skin care composition may be used.

In case, the method further comprises the provision of water and at least one oil, the mixing may be carried out in any order. Preferably, the water and the at least one oil are combined and mixed to form a mixture followed by the addition and mixing of the surface-reacted calcium carbonate.

Mixing can be carried out at temperatures typically used for preparing a cosmetic base formulation. Preferably, mixing is carried out at a temperature in the range from 15 to 100° C., more preferably from 20 to 85° C. such as of about 45° C.

The method for the preparation of the cosmetic and/or skin care composition may further comprise the provision of at least one additive. The combining and mixing of the at least one additive and the surface-reacted calcium carbonate may also be carried out under conventional mixing conditions. The skilled man will adapt these mixing conditions (such as the configuration of mixing pallets and mixing speed) according to his process equipment. It is appreciated that any mixing method which would be suitable to form a cosmetic and/or skin care composition may be used.

In case, the method comprises the provision of the surface-reacted calcium carbonate, water and/or at least one oil, and at least one additive, and preferably two or more additives, the combining and mixing may be carried out in any order.

For example, the method for the preparation of the cosmetic and/or skin care composition may comprise the steps of:
a) providing a surface-reacted calcium carbonate as described herein,
b) providing water,
c) providing at least one oil,
d) providing two or more additives,
e) combining and mixing one or more of the two or more additives with water to form a first mixture,
f) combining and mixing one or more of the two or more additives with the at least one oil to form a second mixture
g) combining and mixing the first and the second mixture to form a third mixture,
h) optionally combining and mixing the third mixture with one or more of the two or more additives, to form a fourth mixture,
i) combining and mixing the surface-reacted calcium carbonate with the third mixture of step g) or the fourth mixture of step h).

The scope and interest of the invention will be better understood based on the following examples which are intended to illustrate certain embodiments of the present invention and are non-limitative.

EXAMPLES

1. Measurement Methods

In the following, measurement methods implemented in the examples are described.

Particle Size Distribution

Volume determined median particle size $d_{50}$ (vol) and the volume determined top cut particle size $d_{98}$ (vol) was evaluated using a Malvern Mastersizer 2000 Laser Diffraction System (Malvern Instruments Plc., Great Britain). The $d_{50}$ (vol) or $d_{98}$ (vol) value indicates a diameter value such that 50% or 98% by volume, respectively, of the particles have a diameter of less than this value. The raw data obtained by the measurement was analyzed using the Mie theory, with a particle refractive index of 1.57 and an absorption index of 0.005. The methods and instruments are known to the skilled person and are commonly used to determine particle size distributions of fillers and pigments.

The weight determined median particle size $d_{50}$ (wt) was measured by the sedimentation method, which is an analysis of sedimentation behaviour in a gravimetric field. The measurement was made with a Sedigraph™ 5120 of Micromeritics Instrument Corporation, USA. The method and the instrument are known to the skilled person and are commonly used to determine particle size distributions of fillers and pigments. The measurement was carried out in an aqueous solution of 0.1 wt.-% $Na_4P_2O_7$. The samples were dispersed using a high speed stirrer and supersonicated.

Specific Surface Area (SSA)

The specific surface area was measured via the BET method according to ISO 9277 using nitrogen, following conditioning of the sample by heating at 250° C. for a period of 30 minutes. Prior to such measurements, the sample was filtered within a Buchner funnel, rinsed with deionised water and dried overnight at 90 to 100° C. in an oven. Subsequently, the dry cake was ground thoroughly in a mortar and the resulting powder was placed in a moisture balance at 130° C. until a constant weight was reached.

Intra-Particle Intruded Specific Pore Volume (in $Cm^3/g$)

The specific pore volume was measured using a mercury intrusion porosimetry measurement using a Micromeritics Autopore V 9620 mercury porosimeter having a maximum applied pressure of mercury 414 MPa (60 000 psi), equivalent to a Laplace throat diameter of 0.004 μm (~nm). The equilibration time used at each pressure step was 20 seconds. The sample material was sealed in a 5 $cm^3$ chamber powder penetrometer for analysis. The data were corrected for mercury compression, penetrometer expansion and sample material compression using the software Pore-Comp (Gane, P. A. C., Kettle, J. P., Matthews, G. P. and Ridgway, C. J., "Void Space Structure of Compressible Polymer Spheres and Consolidated Calcium Carbonate Paper-Coating Formulations", Industrial and Engineering Chemistry Research, 35(5), 1996, p 1753-1764.).

The total pore volume seen in the cumulative intrusion data can be separated into two regions with the intrusion data from 214 μm down to about 1-4 μm showing the coarse packing of the sample between any agglomerate structures contributing strongly. Below these diameters lies the fine inter-particle packing of the particles themselves. If they also have intra-particle pores, then this region appears bi-modal, and by taking the specific pore volume intruded by mercury into pores finer than the modal turning point, i.e. finer than the bi-modal point of inflection, the specific intra-particle pore volume is defined. The sum of these three regions gives the total overall pore volume of the powder, but depends strongly on the original sample compaction/settling of the powder at the coarse pore end of the distribution.

By taking the first derivative of the cumulative intrusion curve the pore size distributions based on equivalent Laplace diameter, inevitably including pore-shielding, are revealed. The differential curves clearly show the coarse agglomerate pore structure region, the inter-particle pore region and the intra-particle pore region, if present. Knowing the intra-particle pore diameter range it is possible to subtract the remainder inter-particle and inter-agglomerate pore volume from the total pore volume to deliver the desired pore volume of the internal pores alone in terms of the pore volume per unit mass (specific pore volume). The same principle of subtraction, of course, applies for isolating any of the other pore size regions of interest.

Oil Absorption

The oil absorption value was determined in according to ISO 787-5:1980.

Coating of Contrast Cards

Contrast cards were coated by using the respective coating compositions and applying them with a coater gap of 50 μm on the surface of the contrast card. The contrast cards used are Leneta contrast cards, form 3-B-H, size 7⅝×11⅜ (194×289 mm), sold by the company Leneta, and distributed by Novamart, Stafa, Switzerland.

Determination of Colour Values (Rx, Ry, Rz)

The colour values Rx, Ry, Rz are determined over the white and black fields of the Leneta contrast card, and are measured with a spectraflas SF 450 X spectrophotometer of the company Datacolor, Montreuil, France.

Contrast Ratio (Opacity) of the Surface of a Coated Contrast Card

Contrast ratio values are determined according to ISO 2814 at a spreading rate of approx. 20 $m^2/l$.

The contrast ratio is calculated as described by the equation below:

$$\text{Contrast ratio } [\%] = \frac{Ry_{black}}{Ry_{white}} \times 100\%$$

with $Ry_{black}$ and $Ry_{white}$ being obtained by the measurement of the color values.

Measurements of Skin Glossiness and Mattifying Power

A Skin-Glossymeter® GL200 probe (of the company Courage & Khazaka) was used for the determination of the mattifying power. Mode of operation: head parallel white light is sent in a 60-degree angle to the skin surface. Part of the light is directly reflected in the same angle (=angle of reflection) and part of the light is absorbed by the skin surface and then scattered and reflected diffusely. The Skin-Glossymeter® GL200 measures both the portion of directly reflected light, mirrored from the surface, which is related to the gloss and the scattered portion from the surface.

2. Pigment Materials

Talc

Micro Talc FC CG AW was supplied by Mondo Minerals, and shows the characteristics listed in Table 1 below.

Boron Nitride

Boroneige® SF-3 was supplied by Merck KGaA, and shows the characteristics listed in Table 1 below.

Titanium Dioxide

The titanium dioxide was supplied by Sigma-Aldrich, and shows the characteristics listed in Table 1 below.

Ground Calcium Carbonate (GCC)

GCC 1 is a high purity natural calcium carbonate obtained from marble, sold by Omya, and shows the characteristics listed in Table 1 below.

GCC 2 is a high purity natural calcium carbonate sold by Omya, and shows the characteristics listed in Table 1 below.

GCC 3 is a high purity natural calcium carbonate obtained from limestone, sold by Omya, and shows the characteristics listed in Table 1 below.

Surface-Reacted Calcium Carbonate

SRCC 1

SRCC 1 had a $d_{50}$ (vol)=6.6 μm, $d_{98}$ (vol)=15.1 μm, SSA=144 $m^2/g$ with an intra-particle intruded specific pore volume of 0.811 $cm^3/g$ (for the pore diameter range of 0.004 to 0.23 μm).

SRCC 1 was obtained by preparing 450 litres of an aqueous suspension of ground calcium carbonate in a mixing vessel by adjusting the solids content of a ground marble calcium carbonate from Hustadmarmor, Norway, having a mass based median particle size distribution of 90% less than 2 μm, as determined by sedimentation, such that a solids content of 16 wt.-%, based on the total weight of the aqueous suspension, is obtained.

Whilst mixing the slurry, 47.1 kg phosphoric acid was added in form of an aqueous solution containing 30 wt.-% phosphoric acid to said suspension over a period of 15 minutes at a temperature of 70° C. After the addition of the acid, the slurry was stirred for additional 5 minutes, before removing it from the vessel and drying.

SRCC 2

SRCC 2 had a $d_{50}$ (vol)=4.5 μm, $d_{98}$ (vol)=8.6 μm, SSA=96.1 $m^2/g$ with an intra-particle intruded specific pore volume of 1.588 $cm^3/g$ (for the pore diameter range of 0.004 to 0.4 μm).

In a mixing vessel, 10 liters of an aqueous suspension of ground limestone calcium carbonate was prepared by adjusting the solids of a ground limestone calcium carbonate having a particle size distribution of 90 wt.-% below 2 µm, based on the total weight of the ground calcium carbonate, such that a solids content of 15 wt.-%, based on the total weight of the aqueous suspension, is obtained.

Whilst mixing the slurry, 2.8 kg phosphoric acid was added in form of an aqueous solution containing 30 wt.-% phosphoric acid to said suspension over a period of 10 minutes. Throughout the whole experiment the temperature of the suspension was maintained at 70° C. After the addition of the acid, the suspension was stirred for additional 5 minutes before removing it from the vessel and drying.

SRCC 3

SRCC 3 has a $d_{50}$=6.6 µm, a $d_{98}$=13.7 µm, a SSA=59.9 $m^2g^{-1}$ and an intra-particle intruded specific pore volume of 0.939 $cm^3/g$ (for the pore diameter range of 0.004 to 0.51 µm).

The SRCC 3 has been prepared as follows:

SRCC 3 was obtained by preparing 350 litres of an aqueous suspension of ground calcium carbonate in a mixing vessel by adjusting the solids content of a ground limestone calcium carbonate from Omya SAS, Orgon having a mass based median particle size of 1.3 µm, as determined by sedimentation, such that a solids content of 10 wt.-%, based on the total weight of the aqueous suspension, is obtained.

Whilst mixing the slurry at a speed of 6.2 m/s, 11.2 kg phosphoric acid was added in form of an aqueous solution containing 30 wt.-% phosphoric acid to said suspension over a period of 20 minutes at a temperature of 70° C. After the addition of the acid, the slurry was stirred for additional 5 minutes, before removing it from the vessel and drying using a jet-dryer.

SRCC 4

SRCC 4 has a $d_{50}$=6.6 µm, $d_{98}$=16.8 µm, a SSA=25.1 $m^2/g$ and an intra-particle intruded specific pore volume of 0.37 $cm^3/g$ (for the pore diameter range of 0.004 to 0.43 µm).

SRCC 4 was obtained by preparing 330 liters of an aqueous suspension of ground calcium carbonate in a mixing vessel by adjusting the solids content of a ground limestone calcium carbonate from Omya SAS, Orgon having a mass based median particle size of 3.0, as determined by sedimentation, such that a solids content of 14.5 wt.-%, based on the total weight of the aqueous suspension, is obtained.

Whilst mixing the slurry at a speed of 12.5 m/s, 7.9 kg phosphoric acid was added in form of an aqueous solution containing 30 wt.-% phosphoric acid to said suspension over a period of 10 minutes at a temperature of 70° C. After the addition of the acid, the slurry was stirred for additional 5 minutes, before removing it from the vessel and drying using a jet-dryer.

SRCC 5

SRCC 5 has a $d_{50}$=1.6 µm, $d_{98}$=10.0 µm, a SSA=31.4 $m^2/g$ and an intra-particle intruded specific pore volume of 0.837 $cm^3/g$ (for the pore diameter range of 0.004 to 0.59 µm).

SRCC 5 was obtained by preparing 7 liters of an aqueous suspension of ground calcium carbonate in a mixing vessel by adjusting the solids content of a ground marble calcium carbonate from Omya Madencilik A. S., Turkey, having a mass based median particle size of 0.4 µm, as determined by sedimentation, such that a solids content of 15 wt.-%, based on the total weight of the aqueous suspension, is obtained.

Whilst mixing the slurry, 290 g phosphoric acid was added in form of an aqueous solution containing 10 wt.-% phosphoric acid to said suspension over a period of 100 minutes at a temperature of 70° C. After the addition of the acid, the slurry was stirred for additional 5 minutes, before removing it from the vessel, filtering the product for removing excess water and then further drying in an oven.

SRCC 6

SRCC 6 has a $d_{50}$=8.6 µm, $d_{98}$=22.0 µm, a SSA=96.1 $m^2/g$ and an intra-particle intruded specific pore volume of 1.73 $cm^3/g$ (for the pore diameter range of 0.004 to 0.34 µm).

SRCC 6 was obtained by preparing 1500 liters of an aqueous suspension of ground calcium carbonate in a mixing vessel by adjusting the solids content of a ground limestone calcium carbonate from Omya SAS, Orgon, having a mass based median particle size of 0.6 µm, as determined by sedimentation, such that a solids content of 10.0 wt.-%, based on the total weight of the aqueous suspension, is obtained.

Whilst mixing the slurry rapidly, 80 kg phosphoric acid was added in form of an aqueous solution containing 20 wt.-% phosphoric acid to said suspension over a period of 60 minutes at a temperature of 62° C. After the addition of the acid, the slurry was stirred for additional 5 minutes, before removing it from the vessel and drying using a jet-dryer.

TABLE 1

Properties of used pigment materials

| Products | $d_{50}$ (µm) | $d_{98}$ (µm) | SSA ($m^2/g$) | Oil Absorption (g/100 g) | R(y) (%) |
|---|---|---|---|---|---|
| SRCC 1 | 6.56 | 15.09 | 144 | 88 | 95.2 |
| SRCC 2 | 4.54 | 8.56 | 96.1 | 105 | 93.0 |
| SRCC 3 | 6.6 | 13.7 | 59.5 | 82 | 92.9 |
| SRCC 4 | 6.6 | 16.8 | 25.1 | 35 | 92.9 |
| SRCC 5 | 1.6 | 10.0 | 31.4 | 44 | 96.4 |
| SRCC 6 | 8.6 | 22.0 | 96.1 | 67 | 91.7 |
| GCC 1 | 2.35 | 10.0 | 3.0 | 14 | 96.4 |
| GCC 2 | 2.85 | 13.0 | 2.6 | 10 | 91.7 |
| GCC 3 | 0.85 | 5.0 | 9.7 | 18 | 91.7 |
| Micro Talc FC CG AW | 8.0 | 26.0 | 6.0 | 37 | 92.0 |
| Boroneige ® SF-3 | 7.49 | 30.0 | 12.5 | 46 | 97.7 |
| Titanium dioxide | 0.45 | 5.0 | 8.3 | 16 | 96.8 |

3. Skin Appearance Modification—Test Results 3.1 Determination of the Covering Power of the Base Composition In order to determine the covering power (coverage) of a pigment material, a base composition comprising different pigment concentrations of the pigment material, namely 5, 10 and 15 wt.-%, were prepared. The covering power of the respective base compositions was determined by measuring the colour values (Rx, Ry, Rz) and then calculation the contrast ratio, as described above.

Table 2 shows the ingredients that were used to prepare a base composition and table 3 shows the ingredients that were used to prepare a cosmetic and/or skin care composition.

In the following the INCI name of some ingredients will be used. INCI stands for International Nomenclature of Cosmetic Ingredients.

TABLE 2

Ingredients for base composition

| Ingredients/trade name | Characterization | Function | Supplier |
|---|---|---|---|
| Bermocoll EHM 200 | Cellulose ether | Thickener | 1) |
| Butyldiglycol acetate | Ester | Film forming agent | 2) |
| Byk 011 | Polymer | Defoamer | 3) |
| Byk 019 | Polyether-modified polydimethylsiloxane | Defoamer | 3) |
| Byk 349 | Polyether-modified siloxane | Surfactant | 3) |
| Calgon N new | Sodium polyphosphate | Dispersing agent | 4) |
| Coapur ™ 2025 | Polyurethane based | Rheology modifier | 5) |
| Disperbyk ®-181 | Alkylolammonium salt of a polyfunctional polymer | Wetting agent | 3) |
| Dowanol ™ DPnB | Dipropylene glycol n-butyl ether | Open time | 6) |
| Ecodis ™ P 90 | Ammonium neutralized polyacrylate | Wetting and dispersing agent | 5) |
| Mergal 723 K | Benzoisothiazolinone | Preservative | 7) |
| Mowilith ® DM 2425, 50% | Aqueous copolymer dispersion based on vinyl acetate | Binding agent | 8) |
| Sodium hydroxide, 10% | Sodium hydroxide solution | pH regulation | 2) |
| Texanol ™ | Isobutyric acid, ester with 2,2,4-trimethyl-1,3-pentanediol | Film forming agent | 9) |

1) Akzo Nobel
2) Diverse (e.g. Sigma-Aldrich)
3) Byk (Altana Group)
4) BK Giulini
5) Coatex (Arkema Group)
6) Dow
7) Troy Chemical Company
8) Celanese
9) Eastman

TABLE 3

Ingredients for a cosmetic and/or skin care composition

| | Ingredients | INCI Nomenclature | Supplier |
|---|---|---|---|
| A) | Aqua dem. | Aqua (Water) | |
| A2 | Vivapur COS 8 | Microcrystalline Cellulose, Cellulose | 10) |
| A3 | Xanthan Gum | Xanthan Gum | 11) |
| B) | Emulium Mellifera | Polyglyceryl-6 Distearate (and) Jojoba Esters (and) Polyglyceryl-3 Beeswax (and) Cetyl Alcohol | 12) |
| | Lanette O | Cetearyl Alcohol | 13) |
| | Imwitor 372 P | Glyceryl Stearate Citrate | 14) |
| | MOD | Octyldodecyl Myristate | 12) |
| | Miglyol 812 | Caprylic/Capric Triglycerides | 15) |
| | Jojoba Oil | Simmondsia Chinensis (Jojoba) Seed Oil | 15) |
| | Olive Oil | Olea Europaea (Olive) Fruit Oil | 15) |
| | Lipocire A SG | C10-18 Triglycerides | 12) |
| | Eutanol G | Octyldodecanol | 13) |
| | Phenonip | Phenoxyethanol (and) Methylparaben (and) Ethylparaben (and) Propylparaben (and) Butylparaben (and) Isobutylparaben | 16) |
| C) | Cocoate BG | Butylene Glycol Cocoate | 12) |
| | Titanium Dioxide | CI 77891 | 17) |
| | Ferroxide 216 P Red | CI 77491 | 18) |

TABLE 3-continued

Ingredients for a cosmetic and/or skin care composition

| | Ingredients | INCI Nomenclature | Supplier |
|---|---|---|---|
| | Ferroxide 510 P Yellow | CI 77492 | 18) |
| | Ferroxide 78 P Black | CI 77499 | 18) |
| D) | Flavour | Aroma | |

10) J. Rettenmaier & Soehne, Germany
11) Omya Hamburg GmbH, Germany
12) Gattefossé SAS, France
13) BASF Schweiz AG, Switzerland
14) Sasol GmbH, Germany
15) Haenseler AG, Switzerland
16) SLI Chemicals GmbH, Germany
17) Sigma Aldrich, Switzerland
18) Huntsman, Switzerland The base composition contains the ingredients listed in Table 4.

TABLE 4

Ingredients and amounts of base composition

| Ingredients | Weight % (based on total weight of base colour) |
|---|---|
| Demineralised water | 40.0 |
| Calgon N new | 0.2 |
| Bermocoll EHM 200 | 1.0 |
| Sodium hydroxide solution, 10% | 0.6 |
| Byk 011 | 2.0 |
| Texanol | 0.5 |
| Butyldiglycol acetate | 0.5 |
| Dowanol ™ DPnB | 1.0 |
| Byk 019 | 0.5 |
| Coapur ™ 2025 | 1.8 |
| Mergal 723 K | 0.2 |
| Demineralized water | 5.0 |
| Ecodis ™ P 90 | 0.6 |
| Disperbyk ®-181 | 1.0 |
| Byk 349 | 0.4 |
| Demineralized water | 14.7 |
| Mowilith ® DM 2425, 50% | 30.0 |
| Total | 100.0 |

The base composition was prepared as follows:

The demineralized water was added to a beaker, then, Calgon, Bermocoll and the sodium hydroxide solution were added under stirring with a lab dissolver until all ingredients were dissolved. Then the other ingredients listed in Table 2 up to Byk 349 were added while continuously stirring the mixture. Then the demineralized water was added and the resulting mixture was thoroughly mixed. Finally, the binding agent Mowilith was added during continuous stirring of the mixture at a speed of 100 rpm to obtain the final base colour.

This base composition was used for the preparation of formulations with different pigment concentrations according to the formulae listed in Table 5:

TABLE 5

Formulations with different pigment concentrations

| Powder with X % pigment concentration | Amount of base colour [wt.-%] | Amount of pigment material [wt.-%] |
|---|---|---|
| Powder with 5% pigment concentration | 95.0 | 5.0 |

TABLE 5-continued

Formulations with different pigment concentrations

| Powder with X % pigment concentration | Amount of base colour [wt.-%] | Amount of pigment material [wt.-%] |
|---|---|---|
| Powder with 10% pigment concentration | 90.0 | 10.0 |
| Powder with 15% pigment concentration | 85.0 | 15.0 |

The formulations were prepared by weighing the respective pigment material in the required amount and adding the respective amount of the base composition. Then the resulting mixtures were homogenized for 1 minute by use of a speed mixer at a speed of 3000 rpm. Then the mixture was mixed using a spatula and subsequently the mixture was again homogenized for 1 minute by use of a speed mixer at a speed of 3000 rpm. The resulting mixture was then used for the measurement of the colour values (Rx, Ry, Rz) which in turn were used for the calculation of the contrast ratio.

The contrast ratio (coverage) values for the used pigment materials at the different pigment concentrations are listed in Table 6.

TABLE 6

Coverage values for the different pigment materials and for different pigment concentrations in a base composition

| | Coverage (%) Percentage of pigment material (%) | | |
|---|---|---|---|
| Products | 5 | 10 | 15 |
| SRCC 1 | 6.6 | 21.3 | 44.6 |
| SRCC 2 | 8.9 | 54.3 | 73.9 |
| SRCC 3 | 6.7 | 24.6 | 53.8 |
| GCC 1 | 3.1 | 4.8 | 5.8 |
| GCC 2 | 3.1 | 4.8 | 5.8 |
| Micro Talc FC CG AW | 4.5 | 5.8 | 6.4 |
| Boroneige ® SF-3 | 16.9 | 32.4 | 45.6 |
| Titanium Dioxide | 29.4 | 51.2 | 62.9 |

The above results clearly show that the inventive surface-reacted calcium carbonates SRCC 1, SRCC 2, and SRCC 3, at pigment concentrations of 10 or 15%, have comparable or even better coverage values when compared to Boroneige® SF-3 that is used in prior art cosmetic formulations for this purpose. The best coverage shows SRCC 2. The coverage is even better than that of titanium dioxide.

3.2 Determination of the Covering Power in a 50/50 Mixture of Base Composition and Cosmetic and/or Skin Care Composition In order to determine the covering power (coverage) of 50/50 mixture of a base composition and a cosmetic and/or skin care composition, cosmetic and/or skin care composition with different pigment material as well as with different pigment material concentrations were prepared. The specific amounts of ingredients of the different cosmetic and/or skin care compositions are shown in Table 7 (general formulation of the cosmetic and/or skin care composition) and Table 8 listing the different pigment materials as well as their concentrations in each cosmetic and/or skin care composition.

The cosmetic and/or skin care compositions were prepared according to the following scheme:

Under rapid mixing (Eurostar 20 high speed control, IKA, 1 000 rpm) disperse A2 into the water (A1) for 10 minutes, then add A3 and disperse for another 10 minutes Pour all ingredients of phase B and heat phases A and B, separately, to a maximum temperature of 70° C.

Mix phase C using a mixer or a three-roll mill (Ultra Turrax T25-D, IKA, 24 000 rpm). Add phase D to phase C when the oil absorption of the pigment material is below 50 g/100 g. If the oil absorption of the pigment material is above 50 g/100 g then it has to be added at later stage of the procedure, Under rapid mixing (Eurostar 20 high speed control, IKA, 3 000 rpm) add phase B to phase A Maintain the rapid mixing and add phase C at a temperature of 40° C., Add separately phase D (if not already added) and phase E at a temperature of 30° C., Allow the resulting mixture to cool to room temperature

TABLE 7

Foundation formulation with type and amount of ingredients

| | Ingredients | % w/w |
|---|---|---|
| A1) | Aqua dem. | add. 100 (*) |
| A2) | Vivapur COS 8 | 1.20 |
| A3) | Xanthan Gum | 0.20 |
| B) | Emulium Mellifera | 4.00 |
| | Lanette O | 1.00 |
| | Imwitor 372 P | 0.10 |
| | MOD | 2.00 |
| | Miglyol Oil | 6.00 |
| | Jojoba Oil | 2.00 |
| | Olive Oil | 1.00 |
| | Lipocire A SG | 3.00 |
| | Eutanol G | 3.00 |
| | Phenonip | 1.00 |
| C) | Cocoate BG | 6.50 |
| | Titanium Dioxide | 4.00 |
| | Ferroxide 216 P red | 0.57 |
| | Ferroxide 510 P yellow | 1.14 |
| | Ferroxide 78 P black | 0.05 |
| D) | Pigment materials | X.00 |
| E) | Flavor | 0.30 |
| Total | | 100.00 |

(*) The water is added in an amount so that the total sum of the weight of all ingredients in the respective foundation is equal to 100.00 wt.-%.

TABLE 8

Amount X.00 and nature of pigment material used in the respective cosmetic and/or skin care composition of Table 7

| | Pigment Material (nature and amount X.00 (w/w %)) | | | | | | | |
|---|---|---|---|---|---|---|---|---|
| Composition No. | SRCC 1 | SRCC 3 | SRCC 2 | GCC 1 | GCC 2 | Micro Talc | Boroneige | TiO$_2$ |
| 1 A | 5.0 | | | | | | | |
| 2 A | | 5.0 | | | | | | |
| 3 A | | | 5.0 | | | | | |
| 4 A | | | | 5.0 | | | | |

TABLE 8-continued

Amount X.00 and nature of pigment material used in the respective cosmetic and/or skin care composition of Table 7

Pigment Material (nature and amount X.00 (w/w %))

| Composition No. | SRCC 1 | SRCC 3 | SRCC 2 | GCC 1 | GCC 2 | Micro Talc | Boroneige | TiO$_2$ |
|---|---|---|---|---|---|---|---|---|
| 5 A  |  |  |  | 10.0 |  |  |  |  |
| 6 A  |  |  |  | 15.0 |  |  |  |  |
| 7 A  |  |  |  |  | 5.0 |  |  |  |
| 8 A  |  |  |  |  | 10.0 |  |  |  |
| 9 A  |  |  |  |  | 15.0 |  |  |  |
| 10 A |  |  |  |  |  | 5.0 |  |  |
| 11 A |  |  |  |  |  | 10.0 |  |  |
| 12 A |  |  |  |  |  |  | 5.0 |  |
| 13 A |  |  |  |  |  |  |  | 4.0 |
| 14 A |  |  | 3.0 |  |  |  |  |  |
| 15 A |  |  | 3.0 |  | 5.0 |  |  |  |

50 wt.-% of the respective cosmetic and/or skin care composition was then mixed with 50 wt.-% of the base composition shown in Table 4. (SpeedMixer DAC 150.1 FVZ, Hauschild Engineering, 3 000 rpm).

The covering power of the resulting 50/50 mixtures was determined by measuring the colour values (Rx, Ry, Rz) followed by calculation the contrast ratio, as described above. The results for the respective compositions are listed in Table 9.

TABLE 9

Covering power (%) and the R(y) value measured for the respective 50/50 mixtures of base composition and cosmetic and/or skin care composition

| 50/50 Mixture of base composition & cosmetic and/or skin care composition Mixture No. | Covering power (%) | R(y) (%) |
|---|---|---|
| 1 B  | 42.5 | 19.4 |
| 2 B  | 43.0 | 19.2 |
| 3 B  | 52.7 | 22.4 |
| 4 B  | 26.1 | 13.3 |
| 5 B  | 33.5 | 16.1 |
| 6 B  | 38.1 | 17.6 |
| 7 B  | 31.9 | 13.9 |
| 8 B  | 39.8 | 17.8 |
| 9 B  | 34.1 | 16.4 |
| 10 B | 37.7 | 18.2 |
| 11 B | 40.8 | 17.1 |
| 12 B | 39.8 | 19.8 |
| 13 B | 27.5 | 13.4 |
| 14 B | 29.3 | 15.4 |
| 15 B | 34.2 | 17.2 |

The 50/50 mixtures including the inventive surface-reacted calcium carbonates (1B, 2B, 3B, 14B and 15B) all show a better coverage power when compared to 50/50 mixtures containing other pigment materials, such as ground calcium carbonate, Boroneige and Micro Talc, at the same pigment concentration.

3.3 Mattifying Power of the Cosmetic and/or Skin Care Composition

The formulations shown in Table 10 have been tested:

TABLE 10

Mattifying formulation with type and amount of ingredients

| | Ingredients [Supplier] | INCI Nomenclature | F01 % w/w | F02 % w/w |
|---|---|---|---|---|
| A) | Lanette O [8] | Cetearyl Alcohol | 2.00 | 2.00 |
|    | Imwitor 372P [1] | Glyceryl Stearate Citrate | 5.00 | 5.00 |
|    | Almond Oil [3] | Prunus Amygdalus Dulcis (Sweet Almond) Oil | 2.00 | 2.00 |
|    | Apricot Oil [3] | Prunus Armeniaca Kernel Oil | 3.00 | 3.00 |
|    | KCC SF1000N - 100 cSt [2] | Polydimethylsiloxane | 2.00 | 2.00 |
|    | KCC 4130P [2] | Stearyl Dimethicone | 2.00 | 2.00 |
|    | Coconut Oil [7] | Cocos nucifera Oil | 3.00 | 3.00 |
| B) | Water dem. | Aqua (water) | add. 100 | add. 100 |
|    | 1,2-Propanediol | Propylene Glycol | 4.00 | 4.00 |
|    | Glycerin | Glycerin | 3.00 | 3.00 |
|    | Xanthan Gum [5] | Xanthan Gum | 0.20 | 0.20 |
|    | Potassium Sorbate [8] | Potassium Sorbate | 1.00 | 1.00 |
|    | Sodium Chloride | Sodium Chloride | 1.00 | 1.00 |
| C) | GCC 3 |  | 5.00 |  |
|    | SRCC 5 |  |  | 5.00 |
| D) | Phenonip | Methylparaben (and) Ethylparaben (and) Butylparaben (and) Propylparaben (and) Phenoxyethanol | 1.00 | 1.00 |
|    |  |  | 100.00 | 100.00 |

[1] Sasol GmBH, Germany
[2] KCC Silicone Corporation, Korea
[3] Hänseler AG, Switzerland
4 Sigma Aldrich, Switzerland
[5] Omya Hamburg GmbH, Germany
6 SLI Chemicals GmbH, Germany
[7] Georges Walther AG, Switzerland
[8] Cognis GmbH, Germany Results of the Mattifying Test:

Results for formulation F01 based on GCC 3 are shown in Table 11.

TABLE 11

Results for formulation F01 based on GCC 3

| Kinetic | Gloss rate Δ (mean ± SEM) | Δ % on mean | Student t-test p | Significance | % of subjects with the expected effect |
|---|---|---|---|---|---|
| Δ D 28 | −0.7 ± 0.3 | −8% | 0.028 | Yes | 67 |

Under these study conditions, after 28 days of once daily use, the formulation F01 based on GCC 3 maintained the skin not shiny, characterized by a decrease of the gloss rate of 8% on average. Less shiny skin was observed in 67% of the subjects.

Results for formulation F02 based on SRCC 5 are shown in Table 12.

TABLE 12

Results for formulation F02 based on SRCC 5

| Kinetic | Gloss rate Δ (mean ± SEM) | Δ % on mean | Student t-test p | Significance | % of subjects with the expected effect |
|---|---|---|---|---|---|
| Δ D 28 | −1.1 ± 0.2 | −12% | <0.001 | Yes | 91 |

Under these study conditions, after 28 days of once daily use, the formulation F02 containing SRCC 5 maintained the skin not shiny, characterized by a significant decrease of the gloss rate of 12% on average. Less shiny skin was observed in 91% of the subjects. Thus, it can be gathered from the results presented in Tables 11 and 12 that the formulation based on surface-reacted calcium carbonate provides a better mattifying effect than the formulation based on ground calcium carbonate.

3.4 Skin Feel Modification—Cosmetic and/or Skin Care Composition Comprising Mint Oil Cosmetic and/or Skin Care Composition Containing Mint Oil Mint oil was loaded onto the surface of GCC 1 and SRCC 3 using a Lödige mixer. Depending on the weight percentage of the mint oil, both calcium carbonates were used in an oil in water emulsion. High quantity of mint oil, exactly 83.2 wt.-%, based on the weight of the surface-reacted calcium carbonate, was loaded on SRCC 3. 1 and 2 wt.-% of the loaded SRCC 3, based on the weight of the skin care composition, was used for formulating the compositions. Given that GCC 1 contains the lower weight percentage of mint oil with 22.6 wt.-%, the weight percentage of the loaded GCC 1 was adjusted to 2 wt.-%, based on the weight of the skin care composition. To compare the skin feel modification between all samples, mint oil alone, i.e. not loaded to a calcium carbonate carrier, was added at a concentration of 0.45 wt.-% to another emulsion, in order to get the same final concentration of mint oil in all compositions. Additionally, skin feel modification of a composition comprising SRCC 4 having a lower surface compared to SRCC 3 was evaluated using the primary test. The primary test included the direct application of the loaded SRCCs on the skin, followed by a movement of spreading and circling the material on the skin. All cosmetic and/or skin care compositions were prepared as oil-in-water emulsions.

3.4.1 Sensory Evaluation

Sensory evaluation of the skin care and/or cosmetic composition is a specific method for applying a composition to the skin, in order to analyze the modification of the skin feel upon and after application. To guarantee comparability, the method follows a strict and identical procedure for each step of the test. For carrying out the test, a quantity of composition, approx. 0.075 mL, is applied on the hand or the finger by using a small spoon. Compositions were marked with a rating from 0 to 10, see also explanation of sensory properties in Tables 13 to 17.

Sensory Properties

TABLE 13

| Aspect | |
|---|---|
| Descriptor | Description |
| Separation | It is a visible separation between the both phases. |
| No separation | No separation is sensed between the both phases. |
| Opaque | Under a standard lamp the product does not let light. |
| No opaque | The product is completely transparent under a standard lamp. Transparent means that the light passes through the product. |
| White | Under a standard lamp the product appears white. |
| No white | The product appears as dark brown or it is transparent. |
| Shiny | The product reflects the light under a standard lamp. |
| No shiny | The product is mat and reflects no light under a standard lamp. |

TABLE 14

| Hand movement | |
|---|---|
| Descriptor | Description |
| Fluid | When the product is placed between the thumb and index fingers and that a pressure is applying, there is no holding, flows of the fingers and moves away from the pressure zone. No resistance is felt. |
| No fluid | When the product is placed between the thumb and index fingers and that a pressure is applying, there is no flow between the both fingers and it moves not away from the pressure zone. A resistance is felling. |
| Stringy | When the product is placed between the thumb and index fingers and that a distance is slowly applied between the both fingers, it is a continuous string. It breaks when the distance between the fingers becomes too large. |
| No stringy | When the product is placed between the thumb and index fingers and that a distance is slowly applied between the both fingers, there is no string/elongated filament formed. |

TABLE 14-continued

Hand movement

| Descriptor | Description |
| --- | --- |
| Slippery | When the product is placed between the thumb and index fingers and that a movement of friction is made, there is no resistance. The product makes the movement easier. |
| No slippery | When the product is placed between the thumb and index fingers and that a movement of friction is made, there is a resistance. The product restricts the movement. |

TABLE 15

Spread

| Descriptor | Description |
| --- | --- |
| Fresh | At the first rotation on the hand a fresh sensation is felt comparable to cold water. |
| No fresh | At the first rotation on the hand there is no modification of temperature on the hand. |
| Bleaching | Between 2 and 3 rotations the product makes the skin white. |
| No bleaching | Between 2 and 3 rotations there is no whitening on the hand. |
| Spread | Between 5 and 10 turns on the hand there is a good distribution of product. |
| No spread | Between 5 and 10 turns on the hand there is no repartition of product. |

TABLE 16

After one minute

| Descriptor | Description |
| --- | --- |
| Greasy | When the product is placed between the thumb and index fingers and that a movement of friction is applied, there is no resistance. The products have an oily aspect. |
| No greasy | When the product is placed between the thumb and index finger and that a movement of friction is applied, there is a resistance and no oily aspect. |
| Sticky | By performing a pressure with index finger on the hand, there is an adhesion. |
| No sticky | By performing a pressure with index finger on the hand, there is no adhesion. |
| Soft | Dry and sliding touch is felt by perform of a slippery on the skin. |
| No soft | No dry and sliding touch is felt by perform of a slippery on the skin. |

TABLE 17

After two minutes

| Descriptor | Description |
| --- | --- |
| Penetrating | The product is disappearing and no residue is detected when touching skin after two minutes. |
| No penetrating | There can still a residue be detected when touching skin after two minutes. |

The following compositions were used:
Composition 1: 0.45% mint oil
Composition 2: 2% SRCC 3 loaded with 83.2 wt.-% mint oil
Composition 3: 1% SRCC 3 loaded with 83.2 wt.-% mint oil
Composition 4: 2% GCC 1 loaded with 22.6 wt.-% mint oil
Composition 5: 1% SRCC 4 loaded with 58.0 wt.-% mint oil The results of the sensory evaluation for the storage at room temperature are shown in Table 18.

TABLE 18

Results of the sensory evaluation for the storage at room temperature

| | Composition No. | | | | |
| --- | --- | --- | --- | --- | --- |
| | 1 | 2 | 3 | 4 | 5 |
| ASPECT | | | | | |
| Opacity | 6 | 9 | 8 | 9 | 9 |
| Whiteness | 4 | 6 | 6 | 9 | 9 |
| Brightness | 7 | 7 | 7 | 6 | 7 |
| HAND MOVEMENT | | | | | |
| Fluidity | 6 | 6 | 5 | 7 | 6 |
| Stringiness | 2 | 1 | 1 | 1 | 1 |
| Slipperiness | 7 | 6 | 8 | 8 | 8 |
| SPREAD | | | | | |
| Freshness | 7 | 10 | 9 | 7 | 10 |
| Bleaching | 5 | 6 | 7 | 5 | 6 |
| Spreadability | 7 | 8 | 8 | 7 | 7 |
| AFTER ONE MINUTE | | | | | |
| Greasiness | 4 | 2 | 3 | 3 | 3 |
| Stickiness | 4 | 2 | 1 | 1 | 1 |
| Softness | 1 | 2 | 3 | 6 | 3 |
| AFTER TWO MINUTES | | | | | |
| Penetrating | 5 | 5 | 5 | 5 | 5 |
| Lasting | 4 | 8 | 7 | 5 | 9 |

TABLE 18-continued

Results of the sensory evaluation for the storage at room temperature

| | Composition No. | | | | |
|---|---|---|---|---|---|
| | 1 | 2 | 3 | 4 | 5 |
| OTHERS | | | | | |
| Odor | Ok (but mint oil does not cover the odor of raw materials) | Ok (odor of raw materials is covered after opening the beaker and application on skin) | Ok (odor of raw materials is covered after opening the beaker and application) | OK (odor of raw materials is covered after opening the beaker and application) | Ok (odor of raw materials is covered after opening the beaker and application on the skin) |
| Viscosity in Cps at 25° C., after 30 s | 32 200 | 32 800 | 39 940 | 21 640 | 34 550 |

Interpretation of Results

Mint oil is currently used in cosmetic compositions as a fragrance component. The concentration used in prior art compositions usually ranges from 0.25 to 1 wt.-% of mint oil, for example, in refreshing creams and lotions. This is comparable to composition 1. As can be gathered from the results of the sensory evaluation, a composition comprising a small quantity of loaded SRCC 3 (1 or 2 wt.-%; see compositions 2 and 3) improves many parameters. For example, opacity and whiteness of compositions comprising SRCC 3 are increased. Compositions comprising SRCC 3 show the best results of freshness during the first application. Furthermore, the compositions based on SRCC 3 are non-greasy and sticky during and/or after application. The skin feel modification is long lasting, i.e. for two to five minutes, when the composition comprises SRCC 3. SRCC 3 is able to deliver a cooling effect during a long time and to feel a pleasant sensation after application. The SRCC 3 has the capacity to conceal the odor of raw ingredients. It has the advantage to take out the fragrance at the end after formulating.

Results show that the freshness sensation was higher when the composition comprises SRCC 3, which indicates that the low proportion of SRCC 3 might have enhanced mint oil liberation and penetration into the skin, increasing freshness perception. No significant differences in freshness intensity after 2 minutes of application were found between compositions containing only mint oil or loaded GCC 1. Loaded SRCC 3 contributes to the immediate perception of freshness and it is not only a skin feel modifier, but a carrier for oils too.

It has been shown that SRCC 3 acts on several different skin feel parameters. The compositions comprising SRCC 3 are easy to spread and show a pleasant feeling during and/or after application. Compositions comprising SRCC 3 reduce dryness, improve mattifying effect, and show the ability to smooth out lines and wrinkles, i.e. the skin appears without blemishes.

SRCC 4 was loaded with 58 wt.-% of mint oil, based on the total weight of the SRCC. To compare its performance, the same quantity, i.e. 58 wt.-% of mint oil, was loaded on SRCC 3. SRCC 4 has a lower surface. It was selected to evaluate the skin feel characteristics and to determine how much oil can be loaded onto the surface-reacted calcium carbonate. The above-described primary test was carried out. Freshness feeling was further intensified for the loaded SRCC 4 compared to loaded SRCC 3. This might be due to the lower surface area and/or lower surface porosity of the SRCC 4. This might in turn result in a smaller quantity of mint oil being adsorbed and/or absorbed onto SRCC 4. The mint oil would be more exposed to the skin surface, and that might be reason why the freshness evaluation is rated as higher. Use of loaded SRCC 4 assures a long lasting skin feel modification, i.e. for two to five minutes. Loaded SRCC 3 also offers a good freshness lasting over a long period of time, but the time period is shorter than with loaded SRCC 4. Slipperiness, softness and spreadability are slightly better for SRCC 4. SRCC 4 is easier to spread and soft to the skin.

Mint oil loading onto the surface of SRCC 4 demonstrated that skin feeling, especially freshness sensation, can be improved and intensified using a SRCC having a lower surface area.

3.5 Skin Feel Modification—Skin Care and/or Cosmetic Composition in Form of a Lipstick The performance of ground calcium carbonate (GCC) and surface-reacted calcium carbonate (SRCC) has been compared. Lipsticks were prepared with the ingredients shown in Table 19. The amount of GCC or SRCC, respectively, is indicated below.

TABLE 19

Lipstick formulation with type and amount of ingredients

| Ingredients [Supplier] | INCI Nomenclature | % w/w |
|---|---|---|
| A) Beeswax [3] | Cera Flava (Beeswax) | 7.00 |
| Carnauba wax [3] | Copernicia Cerifera (Carnauba) Wax | 5.00 |
| Candelilla wax [3] | Euphorbia Cerifera (Candelilla) Wax | 8.00 |
| Jojoba oil [4] | Simmondsia Chinensis (Jojoba) Seed Oil | 5.00 |
| Apricot kernel oil [2] | Prunus Armeniaca (Apricot) Kernel Oil | 5.00 |
| Ricin Oil [3] | Ricinus Communis (Castor) Seed Oil | 28.40 |
| Almond Oil [4] | Prunus Amygdalus Dulcis (Sweet Almond) Oil | 10.00 to 19.00[1] |
| Coconut Oil [6] | Cocos Nucifera Oil | 15.00 |
| Submica M [1] | Mica | 2.00 |
| GCC or SRCC | | 1.00 to 10.00[1] |
| Carmine Lake 50% | C.I. 75470 | 6.00 |

TABLE 19-continued

Lipstick formulation with type and amount of ingredients

| | Ingredients [Supplier] | INCI Nomenclature | % w/w |
|---|---|---|---|
| B) | DL-α-tocopheryl acetate [5] | Tocopheryl Acetate | 0.30 |
| | Flavor | Aroma | q.s |
| | | | 100.00 |

[1]The amount of almond oil was adapted based on the used amount of GCC or SRCC to a combined amount of almond oil and GCC or SRCC of 20 wt. %, based on the total weight of the composition.
[1] Omya Hamburg GmbH; Germany
[2] Gustav Heess; Germany
[3] Georges Walther AG; Switzerland
[4] Hänseler AG; Switzerland
[5] Sigma Aldrich; Switzerland
[6] Mimox AG; Switzerland Phase A is heated to 80° C. in a glass beaker until homogeneous.
Add phase B components to phase A while stirring gently. Homogenize the mixture (Ultra Turrax T25-D, IKA, 24 000 rpm)
Then pour the liquid mixture into the appropriate molds and place the molds in the refrigerator overnights.
Place the molds at room temperature and wait 1 hour.
Remove the lipstick from the molds.
The following amounts of GCC 2 or SRCC 2 were used for the compositions as described in Table 19:
Composition 1: 2 wt. % SRCC 2
Composition 2: 5 wt. % GCC 2
Composition 3: 10 wt. % GCC 2
Composition 4: w/o filler (i.e. 20 wt.-% almond oil)
Composition 5: 1 wt. % SRCC 2
Sensory evaluation was carried out according to the criteria shown in tables 20 to 22.

TABLE 20

Aspect

| Descriptor | Description |
|---|---|
| Defect on the lipstick | If there are exudation, blooming or bubbles on the surface of the lipstick |
| No homogeneous | The lipstick shows some irregularities |
| Homogeneous | The surface of the lipstick is even |
| No shiny | The lipstick looks matt |
| Shiny | The appearance of the lipstick is shiny |
| No smooth | The surface of the lipstick appears irregular |
| Smooth | The surface of the lipstick looks smooth, without any irregularities |

TABLE 21

Hand movement (on the hand)

| Descriptor | Description |
|---|---|
| No hard | Breaking easily, bend or crumble during application |
| Hard | The stick has a good rigidity/strength |
| No homogeneous | The film is not homogeneous and does not cover the skin |
| Homogeneous | An uniform film is gotten during application |
| Slippery | When the lipstick is applied on the hand, it makes the movement easier |
| No slippery | When the lipstick is applied on the hand, it restricts the movement |
| Coverage (only visual) | The lipstick covers the skin. |
| Color strength | Only visual determination |

TABLE 22

Spread (on lip)

| Descriptor | Description |
|---|---|
| No smooth | The film is not homogeneous and rough |
| Smooth | No grainy feeling |
| Not messy | Pigments are not smeary on lip |
| Messy | Pigments leave some marks on lip |
| No spread | It is difficult to apply the lipstick, it is not uniform et doesn't remain on lips |
| spread | Pigment spread easily, evenly and stick on the lip once applied |
| No shiny | It has glossy effect on lip |
| Shiny | It looks shiny on lip |
| No greasy | No oily feeling after application |
| Greasy | Feel oily on lip after use |

Results of the sensory evaluation are shown in Table 23. Table 24 shows the results of the color evaluation.

TABLE 23

Results of the sensory evaluation

| | Composition-No. | | | | |
|---|---|---|---|---|---|
| | 1 | 2 | 3 | 4 | 5 |
| ASPECT | | | | | |
| Defect on the lipstick | — | — | — | — | *2 |
| Homogeneity | 8 | 7 | 7 | 6 | 6 |
| Brightness | 5 | 3 | 2 | 6 | 5 |
| Smoothness | 6 | 8 | 8 | 8 | 8 |
| HAND MOVEMENT (ON THE HAND) | | | | | |
| Hardness | 8 | 7 | 8 | 5 | 7 |
| Homogeneity | 9 | 6 | 6 | 3 | 7 |
| Slippery | 5 | 7 | 7 | 5 | 7 |
| Coverage (only visual) | 9 | 7 | 8 | 4 | 7 |
| Color strength | 9 | 7 | 6 | 5 | 5 |
| SPREAD (ON LIP) | | | | | |
| Smoothness | 8 | 7 | 8 | 4 | 8 |
| Messiness | 1 | 1 | 1 | 3 | 1 |
| Spreadability | 7 | 7 | 8 | 3 | 8 |
| Brightness | 8 | 6 | 6 | 8 | 8 |
| Greasiness | 3 | 4 | 3 | 5 | 3 |
| PERCENTAGE OF FILLER (%) | | | | | |
| SRCC 2 | 2 | | | | 1 |
| GCC 2 | | 5 | 10 | | |

TABLE 24

Results of the color evaluation

| | Composition No.. | | | | |
|---|---|---|---|---|---|
| | 1 | 2 | 3 | 4 | 5 |
| COLOR MEASUREMENT | | | | | |
| R (y) | 89.18 | 89.12 | 90.17 | 80.32 | 59.85 |
| PERCENTAGE OF FILLER (%) | | | | | |
| SRCC 2 | 2 | | | | 1 |
| GCC 2 | | 5 | 10 | | |

Interpretation of Results

When the concentration of powders is too high, e.g. above 10 wt. %, the lipstick shows some defects like bubbles, cracks or streaks. Evaluation of homogeneity seems to be better in presence of minerals but it depends on the concentration used. More precisely, the homogeneity is good for concentrations in the range of 2 to 10 wt. %. Hardness of the lipstick correlates with the weight percentage of calcium carbonate present in the lipstick composition. The higher the concentration of the calcium carbonate in the composition is, the higher is the hardness of the prepared lipstick. All lipsticks provide a better homogeneity during application compared to the reference, which does not contain GCC or SRCC. The best homogeneity is provided by composition 1 and 5 comprising SRCC 2. Furthermore, composition 5 comprising 1 wt. % SRCC 2 provides a good slippery. The addition of SRCC to a composition further allows for improving the coverage. SRCC 2 provides a darker color compared to the reference. Smoothness is increased for composition 1 and 5 comprising SRCC 2.

The invention claimed is:

1. A method for modifying skin appearance of a person and/or in modifying the skin feel as perceived by the person comprising applying to the skin of the person a cosmetic and/or skin care composition comprising a surface-reacted calcium carbonate having a volume median particle size $d_{50}$ from 0.1 to 90 µm,
   wherein the surface-reacted calcium carbonate is a reaction product of natural ground calcium carbonate or precipitated calcium carbonate with carbon dioxide and one or more $H_3O^+$ ion donors, wherein the carbon dioxide is formed in situ by the $H_3O^+$ ion donors treatment and/or is supplied from an external source,
   the amount of the surface-reacted calcium carbonate in the cosmetic and/or skin care composition is from 0.1 to 5 wt-% based on the total weight of the cosmetic and/or skin care composition, and
   the method results in the appearance of the skin being modified and/or in modifying the skin feel as perceived by the person.

2. The method of claim 1, wherein the surface-reacted calcium carbonate has a volume median particle size $d_{50}$ from 0.5 to 50 µm.

3. The method of claim 1, wherein the surface-reacted calcium carbonate has a specific surface area of from 15 $m^2/g$ to 200 $m^2/g$, measured using nitrogen and the BET method.

4. The method according to claim 1, wherein
   the natural ground calcium carbonate is selected from the group consisting of marble, chalk, limestone, and mixtures thereof, or
   the precipitated calcium carbonate is selected from the group consisting of precipitated calcium carbonates having an aragonitic, vateritic or calcitic crystal form, and mixtures thereof.

5. The method according to claim 1, wherein the at least one $H_3O^+$ ion donor is selected from the group consisting of hydrochloric acid, sulphuric acid, sulphurous acid, phosphoric acid, citric acid, oxalic acid, an acidic salt, acetic acid, formic acid, and mixtures thereof.

6. The method according to claim 1, wherein the appearance of the skin being modified is by (a) covering and/or opacifying the skin surface, (b) decreasing the gloss and/or shininess of the skin surface, and/or (c) modifying the skin colour.

7. The method according to claim 1, wherein the cosmetic and/or skin care composition has a pH value of ≤8.5.

8. The method according to claim 1, wherein the surface-reacted calcium carbonate is present in the cosmetic and/or skin care composition in an amount from 0.1 to 50 wt.-%, based on the total weight of the composition.

9. The method according to claim 1, wherein the cosmetic and/or skin care composition further comprises water and/or at least one oil.

10. The method according to claim 1, wherein the cosmetic and/or skin care composition comprises at least one active agent being adsorbed onto and/or absorbed into the surface of the surface-reacted calcium carbonate.

11. The method according to claim 10, wherein the at least one active agent is selected from pharmaceutically active agents, biologically active agents, vitamins, disinfecting agents, preservatives, flavouring agents, surfactants, oils, fragrances, essential oils, and mixtures thereof.

12. The method according to claim 1, wherein the composition further comprises at least one additive selected from the group consisting of bleaching agents, thickeners, stabilizers, chelating agents, preserving agents, wetting agents, emulsifiers, emollients, fragrances, colorants, skin tanning compounds, antioxidants, minerals, pigments, UV-A and/or UV-B filter, and mixtures thereof.

13. The method according to claim 1, wherein the cosmetic and/or skin care composition is selected from an eye make-up product, a facial make-up product, a lip care product, a hand care product, a skin care product, or a combination product thereof.

14. The method according to claim 1, wherein the cosmetic and/or skin care composition has a Brookfield viscosity in a range from 4,000 to 50,000 mPas at 25° C.

15. The method according to claim 1, wherein the surface-reacted calcium carbonate provides skin feel modification.

16. The method according to claim 1, wherein the at least one $H_3O^+$ ion donor is selected from the group consisting of hydrochloric acid, sulphuric acid, sulphurous acid, phosphoric acid, oxalic acid, $H_2PO_4^-$, being at least partially neutralised by a cation selected from $Li^+$, $Na^+$ and/or $K^+$, $HPO_4^{2-}$, being at least partially neutralised by a cation selected from $Li^+$, $Na^+$, $K^+$, $Mg^{2+}$, and/or $Ca^{2+}$, and mixtures thereof.

17. The method according to claim 1, wherein the method results in the appearance of the skin being modified such that the appearance of the skin surface is modified by (a) covering and/or opacifying the skin surface and/or (b) decreasing the gloss and/or shininess of the skin surface.

18. The method according to claim 1, wherein the cosmetic and/or skin care composition has a pH value of ≤8.0.

19. The method according to claim 1, wherein the surface-reacted calcium carbonate is present in the cosmetic and/or skin care composition in an amount from 0.5 to 20 wt.-%, based on the total weight of the composition.

20. The method according to claim 1, wherein the cosmetic and/or skin care composition further comprises water, and/or at least one oil selected from the group consisting of vegetable oils and esters thereof, alkanecoconutester, plant extracts, animal fats, siloxanes, silicones, fatty acids and esters thereof, petrolatum, glycerides and pegylated derivatives thereof.

21. The method according to claim 1, wherein the cosmetic and/or skin care composition has a Brookfield viscosity in a range from 10,000 to 45,000 mPas at 25° C.

* * * * *